United States Patent
Himeno et al.

(10) Patent No.: US 12,118,819 B2
(45) Date of Patent: Oct. 15, 2024

(54) FINGERPRINT RECOGNITION SENSOR AND OPTICAL ELEMENT

(71) Applicant: FUJIFILM Corporation, Tokyo (JP)

(72) Inventors: Ryoji Himeno, Kanagawa (JP); Shinichi Morishima, Kanagawa (JP); Yuki Hirai, Kanagawa (JP); Makoto Kamo, Kanagawa (JP); Megumi Sekiguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/474,861

(22) Filed: Sep. 26, 2023

(65) Prior Publication Data

US 2024/0021012 A1    Jan. 18, 2024

Related U.S. Application Data

(63) Continuation of application No. PCT/JP2022/015870, filed on Mar. 30, 2022.

(30) Foreign Application Priority Data

Mar. 30, 2021 (JP) ................. 2021-056929
Sep. 28, 2021 (JP) ................. 2021-157932

(51) Int. Cl.
*G06V 40/13* (2022.01)
*G02B 5/20* (2006.01)

(52) U.S. Cl.
CPC ......... *G06V 40/1318* (2022.01); *G02B 5/208* (2013.01)

(58) Field of Classification Search
CPC .. G02B 5/208; G02B 5/22; G02B 5/30; A61B 5/1172; G01N 21/21; G01N 21/359
See application file for complete search history.

(56) References Cited

U.S. PATENT DOCUMENTS

| | | | |
|---|---|---|---|
| 2005/0169506 A1* | 8/2005 | Fenrich | G06V 40/1324 382/127 |
| 2008/0232653 A1* | 9/2008 | Rowe | A61B 5/6826 382/124 |

(Continued)

FOREIGN PATENT DOCUMENTS

| | | |
|---|---|---|
| JP | 2001-100040 A | 4/2001 |
| JP | 2008-064842 A | 3/2008 |

(Continued)

OTHER PUBLICATIONS

International Search Report issued in PCT/JP2022/015870 on Jun. 21, 2022.

(Continued)

*Primary Examiner* — Jonathan A Boyd
(74) *Attorney, Agent, or Firm* — Edwards Neils LLC; Jean C. Edwards, Esq.

(57) ABSTRACT

A fingerprint recognition sensor having an excellent S/N ratio and capable of realizing thinning and an optical element including the fingerprint recognition sensor. The fingerprint recognition sensor includes a light-receiving element; and an optical element including a near infrared absorbing dichroic substance, in which a fingerprint reading surface is positioned on a side of the optical element opposite to the light-receiving element side. The optical element has an absorption axis with respect to near infrared light in an in-plane direction. When linearly polarized light of near infrared light orthogonal to the absorption axis is radiated from a normal direction of the optical element and from a direction inclined by 45° from the normal direction at an azimuthal angle orthogonal to the absorption axis, an absorbance during the radiation from the direction inclined by 45° from the normal direction is more than an absorbance during the radiation from the normal direction.

7 Claims, 4 Drawing Sheets

(56) References Cited

U.S. PATENT DOCUMENTS

2013/0022248 A1* 1/2013 Rowe ................ G06V 40/1324
                                                    382/124
2017/0277934 A1* 9/2017 Hama ................ G06V 40/1365

FOREIGN PATENT DOCUMENTS

| JP | 2010-522379 A | 7/2010 |
| JP | 2015-197489 A | 11/2015 |
| JP | 2020-122854 A | 8/2020 |
| WO | 2018/216662 A1 | 11/2018 |

OTHER PUBLICATIONS

Written Opinion issued in PCT/JP2022/015870 on Jun. 21, 2022.
International Preliminary Report on Patentability completed by WIPO on Oct. 3, 2023 in connection with International Patent Application No. PCT/JP2022/015870.

* cited by examiner

FINGERPRINT RECOGNITION SENSOR AND OPTICAL ELEMENT

CROSS-REFERENCE TO RELATED APPLICATIONS

This application is a Continuation of PCT International Application No. PCT/JP2022/015870 filed on Mar. 30, 2022, which was published under PCT Article 21(2) in Japanese, and which claims priority under 35 U.S.C. § 119(a) to Japanese Patent Application No. 2021-056929 filed on Mar. 30, 2021 and Japanese Patent Application No. 2021-157932 filed on Sep. 28, 2021. The above applications are hereby expressly incorporated by reference, in their entirety, into the present application.

BACKGROUND OF THE INVENTION

1. Field of the Invention

The present invention relates to a fingerprint recognition sensor and an optical element.

2. Description of the Related Art

As an optical fingerprint recognition device, WO2018/216662A describes a fingerprint recognition device using an unevenness detection device including an optical member that includes a louver film and an imaging element (for example, refer to claim 11 and FIGS. 11 to 13).

SUMMARY OF THE INVENTION

The present inventors conducted an investigation on the fingerprint recognition device described in WO2018/216662A and clarified that, in a case where the optical member including the louver film is used, a signal/noise ratio (S/N ratio) of desired light increases, but it is difficult to thin the fingerprint recognition sensor.

Accordingly, an object of the present invention is to provide a fingerprint recognition sensor having an excellent S/N ratio and capable of realizing thinning and an optical element including the fingerprint recognition sensor.

As a result of conducting a thorough investigation to achieve the above-described object, the present inventors found that, in a case where an optical element including a near infrared absorbing dichroic substance and satisfying predetermined optical characteristics is used, a fingerprint recognition sensor having an excellent S/N ratio and capable of thinning can be prepared, thereby completing the present invention.

That is, the present inventors found that the above-described object can be achieved by employing the following configurations.

[1] A fingerprint recognition sensor comprising:
a light-receiving element; and
an optical element that includes a near infrared absorbing dichroic substance,
in which a fingerprint reading surface is positioned on a side of the optical element opposite to the light-receiving element side,
the optical element has an absorption axis with respect to near infrared light in an in-plane direction, and
in a case where linearly polarized light of near infrared light orthogonal to the absorption axis is radiated from a normal direction of the optical element and from a direction inclined by 45° from the normal direction at an azimuthal angle orthogonal to the absorption axis, an absorbance during the radiation from the direction inclined by 45° from the normal direction is more than an absorbance during the radiation from the normal direction.

[2] The fingerprint recognition sensor according to [1], in which the optical element includes a first layer that includes a near infrared absorbing dichroic substance and has an absorption axis with respect to near infrared light in an in-plane direction and a second layer that includes a near infrared absorbing dichroic substance and has an absorption axis with respect to near infrared light in a thickness direction.

[3] The fingerprint recognition sensor according to [2], in which the first layer and the second layer are layers that do not substantially absorb visible light.

[4] The fingerprint recognition sensor according to [1], in which the optical element consists of a single layer that includes a near infrared absorbing dichroic substance and has an absorption axis with respect to near infrared light in an in-plane direction, and
in a cross-section taken along the absorption axis, the optical element does not have absorption anisotropy with respect to near infrared light.

[5] The fingerprint recognition sensor according to [4], in which the near infrared absorbing dichroic substance is a substance that does not substantially absorb visible light.

[6] The fingerprint recognition sensor according to [4] or [5], in which the near infrared absorbing dichroic substance is a disk-like colorant.

[7] An optical element comprising:
a first layer that includes a near infrared absorbing dichroic substance and has an absorption axis with respect to near infrared light in an in-plane direction; and
a second layer that includes a near infrared absorbing dichroic substance and has an absorption axis with respect to near infrared light in a thickness direction.

[8] An optical element comprising:
an optically-anisotropic layer that is formed of a composition including a near infrared absorbing dichroic substance, a liquid crystal compound, and an alignment control agent,
in which the near infrared absorbing dichroic substance is a disk-like colorant,
the liquid crystal compound is a disk-like liquid crystal compound,
the alignment control agent is an air interface alignment agent,
the disk-like colorant is disposed in a state where the disk-like colorant is aligned to be perpendicular and uniaxial to a surface of the optically-anisotropic layer, and
the disk-like liquid crystal compound is immobilized in a state where the disk-like colorant is aligned to be perpendicular and uniaxial to the surface of the optically-anisotropic layer.

[9] The optical element according to [8], in which the disk-like colorant has a maximal absorption wavelength in a wavelength range of 800 to 1000 nm.

[10] The optical element according to [8] or [9], in which a dichroic ratio in an in-plane direction is 5 or more.

[11] The optical element according to any one of [8] to [10], in which a color is neutral gray.

According to the present invention, it is possible to provide a fingerprint recognition sensor having an excellent S/N ratio and capable of realizing thinning and an optical element including the fingerprint recognition sensor.

DESCRIPTION OF THE PREFERRED EMBODIMENTS

Figure 1:
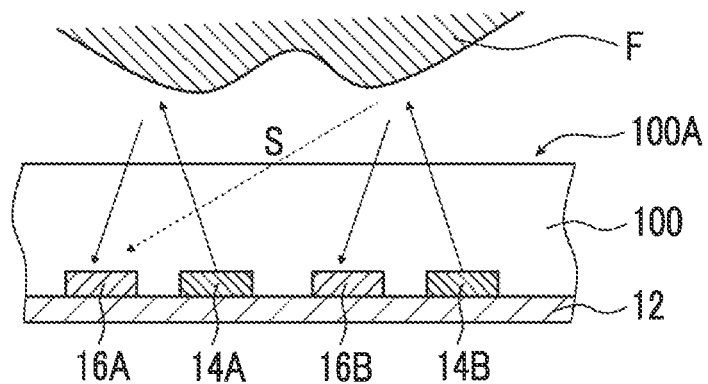
FIG. 1 is a diagram showing one embodiment of a fingerprint recognition sensor in the related art.

Hereinafter, the details of the present invention will be described.

The following description regarding configuration requirements has been made based on a representative embodiment of the present invention. However, the present invention is not limited to the embodiment.

In the present specification, numerical ranges represented by "to" include numerical values before and after "to" as lower limit values and upper limit values.

In addition, in the present specification, the "(meth)acrylic" is a notation representing "acrylic" or "methacrylic".

In addition, in the present specification, a fast axis and a slow axis are each defined at 550 nm unless otherwise specified.

In the present specification, Re(λ) and Rth(λ) represent an in-plane retardation and a thickness-direction retardation at a wavelength λ, respectively. Unless otherwise specified, the wavelength λ refers to 550 nm.

In addition, in the present specification, Re(λ) and Rth(λ) are values measured at the wavelength λ using AxoScan (manufactured by Axometrics, Inc.). By inputting an average refractive index ((nx+ny+nz)/3) and a film thickness (d (μm)) to AxoScan, the following expressions can be calculated.

In-Plane Slow Axis Direction (°)

Re(λ)=R0(λ)

Rth(λ)=((nx+ny)/2−nz)×d

R0(λ) is expressed as a numerical value calculated by AxoScan and represents Re(λ).

In the present specification, the refractive indices nx, ny, and nz are measured using an Abbe refractometer (NAR-4T, manufactured by Atago Co., Ltd.), and a sodium lamp (λ=589 nm) is used as a light source. In addition, the wavelength dependence can be measured using a combination of a multi-wavelength Abbe refractometer DR-M2 (manufactured by Atago Co., Ltd.) and an interference filter.

In addition, as the refractive index, values described in "Polymer Handbook" (John Wiley&Sons, Inc.) and catalogs of various optical films can also be used. The values of average refractive index of major optical films are as follows: cellulose acylate (1.48), cycloolefin polymer (1.52), polycarbonate (1.59), polymethyl methacrylate (1.49), and polystyrene (1.59).

In the present specification, "visible light" refers to light having a wavelength of 400 nm or more and less than 700 nm.

In addition, "near infrared light" refers to light having a wavelength of 700 or more and less than 2500 nm.

In addition, "ultraviolet light" refers to light having a wavelength of 10 nm or more and less than 400 nm.

In the present specification, angles (for example, an angle of "90°" or the like) and a relationship thereof (for example, "orthogonal" or "parallel") includes a range of error that is allowable in the technical field belonging to the present invention. For example, an angle is in a range of the exact angle±10°, and the error from the exact angle is preferably 5° or less and more preferably 3° or less.

[Fingerprint Recognition Sensor]

A fingerprint recognition sensor according to an embodiment of the present invention comprises: a light-receiving element; and an optical element that includes a near infrared absorbing dichroic substance, in which a fingerprint reading surface is positioned on a side of the optical element opposite to the light-receiving element side.

In addition, in the fingerprint recognition sensor according to the embodiment of the present invention, the optical element has an absorption axis with respect to near infrared light in an in-plane direction, and in a case where linearly polarized light of near infrared light orthogonal to the absorption axis is radiated from a normal direction of the optical element and from a direction inclined by 45° from the normal direction at an azimuthal angle orthogonal to the absorption axis, an absorbance during the radiation from the direction inclined by 45° from the normal direction is more than an absorbance during the radiation from the normal direction (hereinafter, also abbreviated as "specific optical element").

Here, regarding the absorption axis in the optical element, in a case where linearly polarized light of near infrared light is radiated from the normal direction of the optical element while changing the azimuthal angle, a direction in which the absorbance is the highest is defined as the absorption axis.

In addition, the absorption axis is derived from the alignment state of the near infrared absorbing dichroic substance.

In addition, the fingerprint reading surface in the fingerprint recognition sensor according to the embodiment of the present invention may be a contact type or a non-contact type.

In the present invention, by using the specific optical element including the near infrared absorbing dichroic substance as described above, a fingerprint recognition sensor having an excellent S/N ratio and capable of thinning can be prepared.

First, hereinafter, the reason why the S/N ratio is poor in the related art will be described in detail.

FIG. 1 is a diagram showing one embodiment of the fingerprint recognition sensor in the related art.

A fingerprint recognition sensor 100 shown in FIG. 1 includes: a substrate 12; and a first light emitting element 14A, a second light emitting element 14B, a first light-receiving element 16A, and a second light-receiving element 16B that are disposed on the substrate 12. The first light emitting element 14A and the first light-receiving element 16A are disposed adjacent to each other, and the second light emitting element 14B and the second light-receiving element 16B are disposed adjacent to each other.

In a case where a finger F of a person approaches a surface 100A side of the fingerprint recognition sensor 100 opposite to the substrate 12, light is radiated as indicated by an arrow from the first light emitting element 14A. The radiated light is reflected from the surface of the finger F. The reflected light is received by the first light-receiving element 16A disposed adjacent to the first light emitting element 14A, and information regarding a fingerprint (surface unevenness) of the finger F can be acquired.

In addition, the light radiated from the first light emitting element 14A is reflected from the finger F, and the reflected light is received by the second light-receiving element 16B. As a result, the information regarding the fingerprint of the finger F can be acquired.

This way, the reflected light that is radiated from a predetermined light emitting element and reflected from the finger F is received by a predetermined light-receiving element. As a result, the fingerprint can be recognized.

On the other hand, in a case where a part of the light that is incident from the second light emitting element 14B and is reflected from the finger F is received by the first light-receiving element 16A as indicated by a broken line in FIG. 1, unevenness information of the fingerprint at a specific position is transmitted to an erroneous position. As a result, the shape of recognized fingerprint varies. Therefore, the fingerprint recognition cannot be accurately performed.

That is, as indicated by a broken line in FIG. 1, stray light S is received by a light-receiving element different from a light-receiving element that should be originally received such that the problem in the related art occurs.

On the other hand, in the present invention, functions described using a first embodiment and a second embodiment described below, that is, the configuration according to claim 1, the effect of the stray light S is suppressed.

First Embodiment

Figure 2:
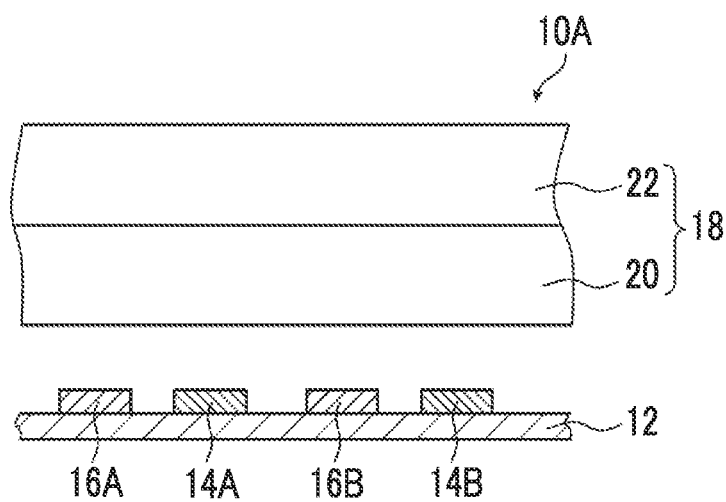
FIG. 2 is a side view showing one example of a first embodiment of a fingerprint recognition sensor according to the present invention.

FIG. 2 is a side view showing one example of a first embodiment of a fingerprint recognition sensor according to the present invention.

A fingerprint recognition sensor 10A shown in FIG. 2 includes: the substrate 12; the first light emitting element 14A, the second light emitting element 14B, the first light-receiving element 16A, and the second light-receiving element 16B that are disposed on the substrate 12; and an optical element 18.

Here, the first light emitting element 14A and the first light-receiving element 16A are disposed adjacent to each other, and the second light emitting element 14B and the second light-receiving element 16B are disposed adjacent to each other.

In addition, the optical element 18 includes a first layer 20 and a second layer 22 in this order from the substrate 12 side. As described below, the first layer 20 and the second layer 22 include a near infrared absorbing dichroic substance, and alignment states thereof are different from each other.

Figure 3A:
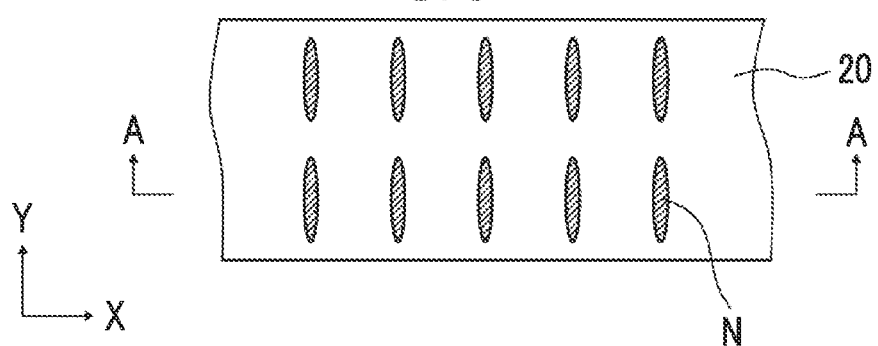
FIG. 3A is a plan view showing a first layer in an optical element shown in FIG. 2.
Figure 3B:
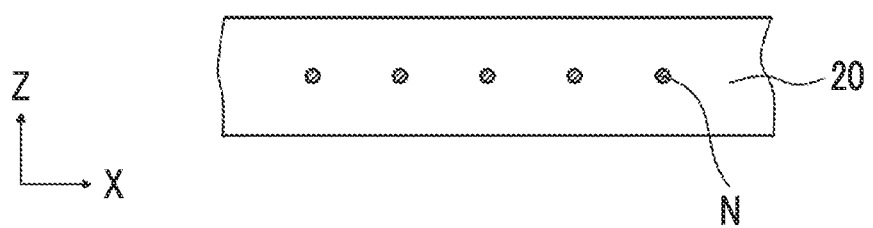
FIG. 3B is a cross-sectional view taken along line A-A of FIG. 3A showing the first layer in the optical element shown in FIG. 2.

FIG. 3A is a plan view showing the first layer 20 in the optical element 18 shown in FIG. 2, and FIG. 3B is a cross-sectional view showing the first layer 20. FIG. 3B is a cross-sectional view taken along line A-A in FIG. 3A.

In FIG. 3A, a direction X and a direction Y represent directions of two coordinate axes orthogonal to each other on an observation surface.

In FIG. 3B, the direction X and a direction Z represent directions of two coordinate axes orthogonal to each other on the observation surface. The direction Z is parallel to a thickness direction of the first layer 20.

As shown in FIGS. 3A and 3B, the first layer 20 includes a near infrared absorbing dichroic substance N.

In addition, as shown in FIGS. 3A and 3B, in the first layer 20, a major axis direction of the near infrared absorbing dichroic substance N is arranged in the Y-axis direction (up-down direction of the paper plane in FIG. 3A).

Therefore, the first layer 20 has an absorption axis with respect to near infrared light in the Y-axis direction of the in-plane direction.

Figure 4A:
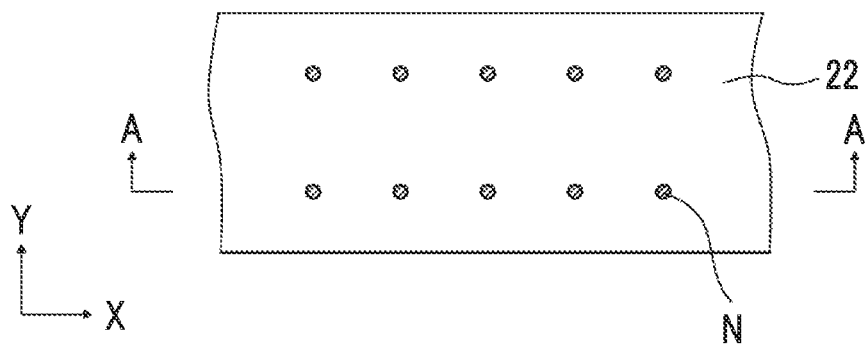
FIG. 4A is a plan view showing a second layer in the optical element shown in FIG. 2.
Figure 4B:
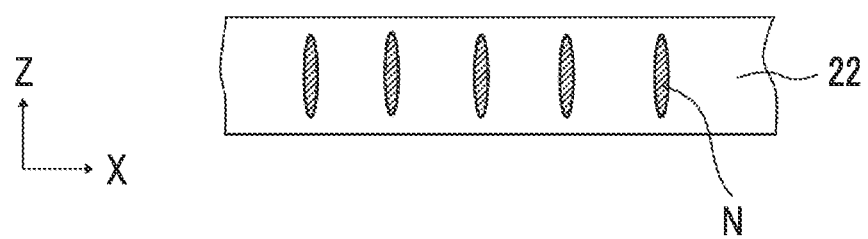
FIG. 4B is a cross-sectional view taken along line A-A of FIG. 3A showing the second layer in the optical element shown in FIG. 2.

FIG. 4A is a plan view showing the second layer 22 in the optical element 18 shown in FIG. 2, and FIG. 4B is a cross-sectional view showing the second layer 22. FIG. 4B is a cross-sectional view taken along line A-A in FIG. 4A.

In FIG. 4A, the direction X and the direction Y represent directions of two coordinate axes orthogonal to each other on the observation surface.

In FIG. 4B, the direction X and the direction Z represent directions of two coordinate axes orthogonal to each other on the observation surface. The direction Z is parallel to a thickness direction of the second layer 22.

As shown in FIGS. 4A and 4B, the second layer 22 includes a near infrared absorbing dichroic substance N.

In addition, as shown in FIGS. 4A and 4B, in the second layer 22, a major axis direction of the near infrared absorbing dichroic substance N is arranged in the Z-axis direction (up-down direction of the paper plane in FIG. 4B).

Therefore, the second layer 22 has an absorption axis with respect to near infrared light in the Z-axis direction (that is, the thickness direction) of the in-plane direction.

As described above, the optical element 18 according to the first embodiment includes: the first layer 20 that has an absorption axis with respect to near infrared light in the in-plane direction; and the second layer 22 that has an absorption axis with respect to near infrared light in the thickness direction.

Figure 5:
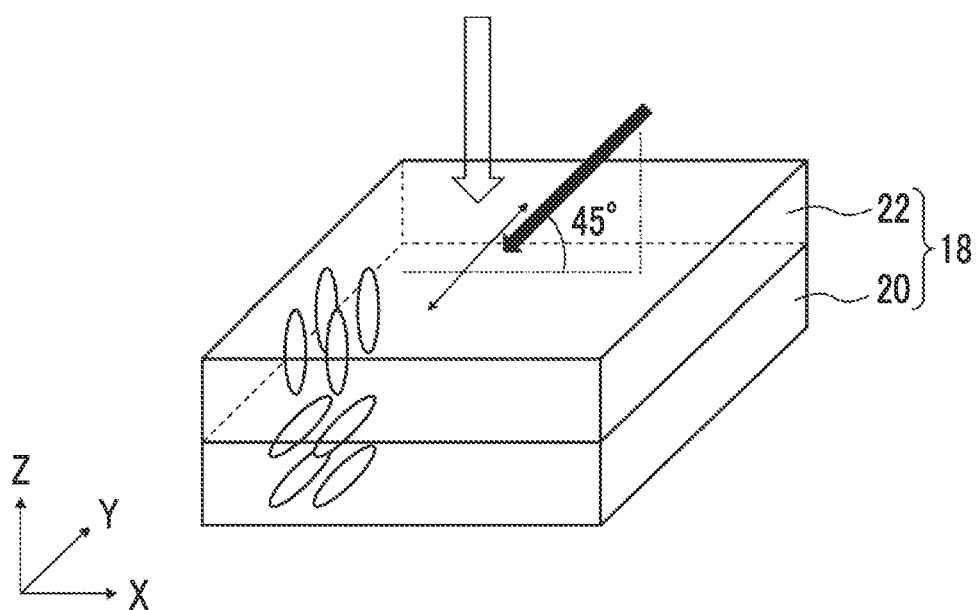
FIG. 5 is a schematic diagram showing a state where linearly polarized light of near infrared light orthogonal to an absorption axis for near infrared light present in an in-plane direction is radiated from a normal direction of the optical element and from a direction inclined by 45° from the normal direction at an azimuthal angle orthogonal to the absorption axis in the first embodiment.

As shown in FIG. 5, the optical element 18 has an absorption axis derived from the first layer 20 in the Y-axis direction of the in-plane direction. That is, the absorption axis is provided in a direction indicated by a thin black arrow.

Next, characteristics in a case where the optical element 18 is irradiated with linearly polarized light of near infrared light orthogonal to the absorption axis will be described.

First, in the optical element 18, the direction of the linearly polarized light of near infrared light orthogonal to the absorption axis corresponds to the X-axis direction.

As shown in a white arrow direction in FIG. 5, in a case where the linearly polarized light is radiated from the normal direction of the optical element 18, the linearly polarized light transmits through the optical element 18 without being absorbed because the absorption axis of the second layer 22 is parallel to the thickness direction and is orthogonal to the absorption axis of the first layer 20.

On the other hand, in a case where the linearly polarized light of near infrared light is radiated from a direction (direction of a thick black arrow in FIG. 5) inclined by 45° from the normal direction at an azimuthal angle (azimuthal angle indicated by a broken line in FIG. 5) orthogonal to the absorption axis of the optical element 18, the absorption axis of the first layer 20 and the absorption axis of the second layer 22 intersect each other in a crossed nicols state. Therefore, light incident from the direction of the thick black arrow is mostly absorbed by the optical element 18 without transmitting through the optical element 18.

That is, in the optical element 18, an absorbance of light incident from the normal direction is more than an absorbance of light incident from the direction inclined by 45° from the normal direction.

Therefore, the optical element 18 has a function of allowing transmission of the light incident from the normal direction and preventing transmission of the light incident from the oblique direction.

Accordingly, in the fingerprint recognition sensor 10A shown in FIG. 2, as described above, by using the optical element 18 including the first layer 20 that has an absorption axis with respect to near infrared light in the in-plane direction and the second layer 22 that has an absorption axis with respect to near infrared light in the thickness direction, the effect of stray light that is the problem in the related art can be suppressed.

Figure 6:
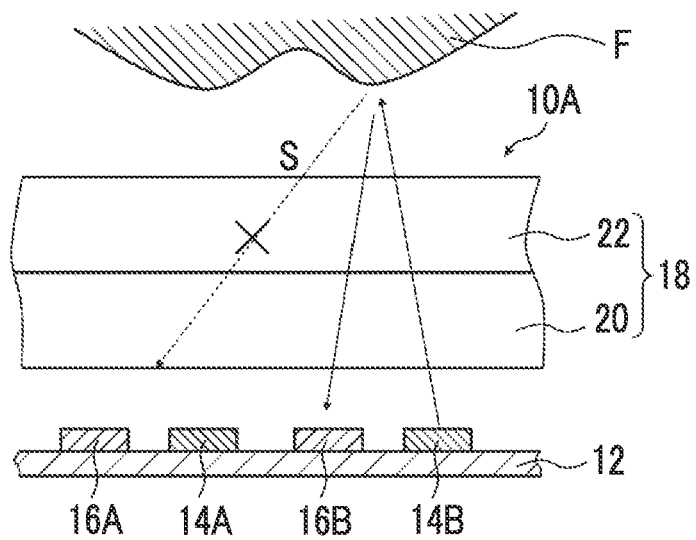
FIG. 6 is a schematic diagram illustrating a mechanism of absorbing stray light S to improve a S/N ratio in the first embodiment of the fingerprint recognition sensor according to the present invention.

Hereinafter, the mechanism will be described using FIG. 6.

As described above, the optical element 18 has a function of allowing transmission of the light incident from the normal direction and preventing transmission of the light incident from the oblique direction. Therefore, in the optical element 18, light that is incident from the second light emitting element 14B, is reflected from the finger F, and travels toward the second light-receiving element 16B is not absorbed, but the stray light S that is a part of the incident from the second light emitting element 14B and reflected from the finger F and travels toward the direction of the first light-receiving element 16A can be absorbed. As a result, the S/N ratio can be improved.

Second Embodiment

Figure 7:
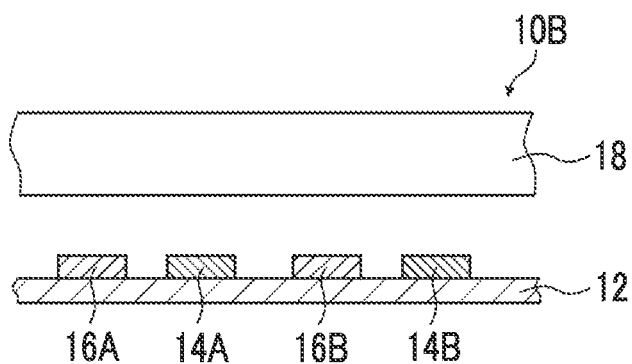
FIG. 7 is a side view showing one example of a second embodiment of the fingerprint recognition sensor according to the present invention.

FIG. 7 is a side view showing one example of the second embodiment of the fingerprint recognition sensor according to the present invention.

A fingerprint recognition sensor 10B shown in FIG. 7 includes: the substrate 12; the first light emitting element 14A, the second light emitting element 14B, the first light-receiving element 16A, and the second light-receiving element 16B that are disposed on the substrate 12; and the optical element 18. The first light emitting element 14A and the first light-receiving element 16A are disposed adjacent to each other, and the second light emitting element 14B and the second light-receiving element 16B are disposed adjacent to each other.

The optical element 18 is a single layer unlike the first embodiment shown in FIG. 2 and includes a near infrared absorbing dichroic substance in a predetermined alignment state as described below.

Figure 8A:
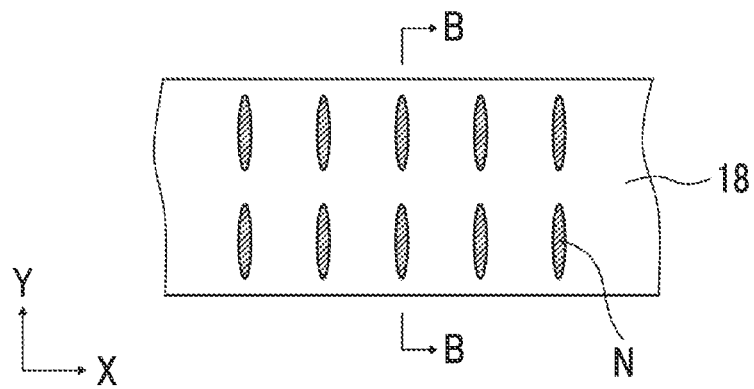
FIG. 8A is a plan view showing the optical element shown in FIG. 7.
Figure 8B:
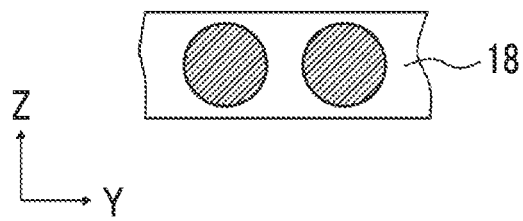
FIG. 8B is a cross-sectional view taken along line B-B of FIG. 8A showing the optical element shown in FIG. 7.

FIG. 8A is a plan view showing the optical element 18 shown in FIG. 7, and FIG. 8B is a cross-sectional view showing the optical element 18. FIG. 8B is a cross-sectional view taken along line B-B in FIG. 8A.

In FIG. 8A, the direction X and the direction Y represent directions of two coordinate axes orthogonal to each other on the observation surface.

In FIG. 8B, the direction Y and the direction Z represent directions of two coordinate axes orthogonal to each other on the observation surface. The direction Z is parallel to the thickness direction of the optical element 18.

As shown in FIGS. 8A and 8B, the optical element 18 includes a near infrared absorbing dichroic substance N.

In addition, as shown in FIG. 8A, in the in-plane direction of the optical element 18, a major axis direction of the near infrared absorbing dichroic substance N is arranged in the Y-axis direction (up-down direction of the paper plane in FIG. 8A). Therefore, an absorption axis with respect to near infrared light in the Y-axis direction is provided in the in-plane direction of the optical element 18.

In addition, as shown in FIG. 8B, in a cross-section taken along the absorption axis, the near infrared absorbing dichroic substance N is arranged in a disk shape. Therefore, in the cross-section taken along the absorption axis with respect to near infrared light in the in-plane direction of the optical element 18, there is no absorption anisotropy with respect to near infrared light.

As described above, the optical element 18 consists of a single layer that has an absorption axis with respect to near infrared light in an in-plane direction, and in a cross-section taken along the absorption axis, the optical element 18 does not have absorption anisotropy with respect to near infrared light.

Figure 9:
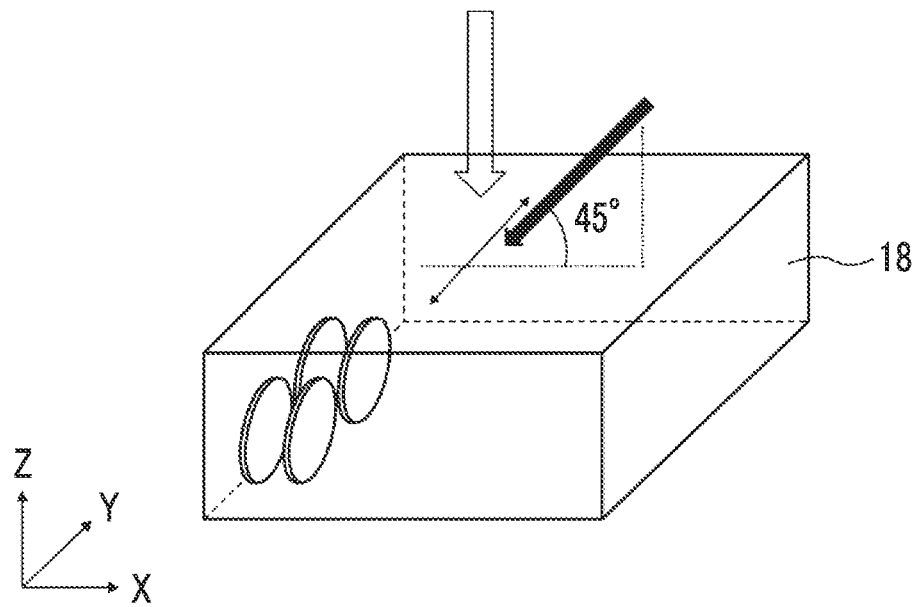
FIG. 9 is a schematic diagram showing a state where linearly polarized light of near infrared light orthogonal to an absorption axis for near infrared light present in an in-plane direction is radiated from a normal direction of the optical element and from a direction inclined by 45° from the normal direction at an azimuthal angle orthogonal to the absorption axis in the second embodiment.

As shown in FIG. 9, in the in-plane direction, the optical element 18 has an absorption axis derived from a side surface of the near infrared absorbing dichroic substance arranged in the disk shape in the Y-axis direction. That is, the absorption axis is provided in a direction indicated by a thin black arrow.

Next, characteristics in a case where the optical element 18 is irradiated with linearly polarized light of near infrared light orthogonal to the absorption axis will be described.

First, in the optical element 18, the direction of the linearly polarized light of near infrared light orthogonal to the absorption axis corresponds to the X-axis direction.

As shown in a white arrow direction in FIG. 9, in a case where the linearly polarized light is radiated from the normal direction of the optical element 18, the linearly polarized light transmits through the optical element 18 without being absorbed because it is orthogonal to the ab sorption axis.

On the other hand, in a case where the linearly polarized light of near infrared light is radiated from a direction (direction of a thick black arrow in FIG. 9) inclined by 45° from the normal direction at an azimuthal angle (azimuthal angle indicated by a broken line in FIG. 9) orthogonal to the absorption axis of the optical element 18, in a cross-section taken along the absorption axis, the optical element 18 does not have absorption anisotropy with respect to near infrared light. Therefore, light incident from the direction of the thick black arrow is mostly absorbed by the near infrared absorbing dichroic substance in the optical element 18 without transmitting through the optical element 18.

That is, in the optical element 18, an absorbance of light incident from the normal direction is more than an absorbance of light incident from the direction inclined by 45° from the normal direction.

Therefore, the optical element 18 has a function of allowing transmission of the light incident from the normal direction and preventing transmission of the light incident from the oblique direction.

Figure 10:
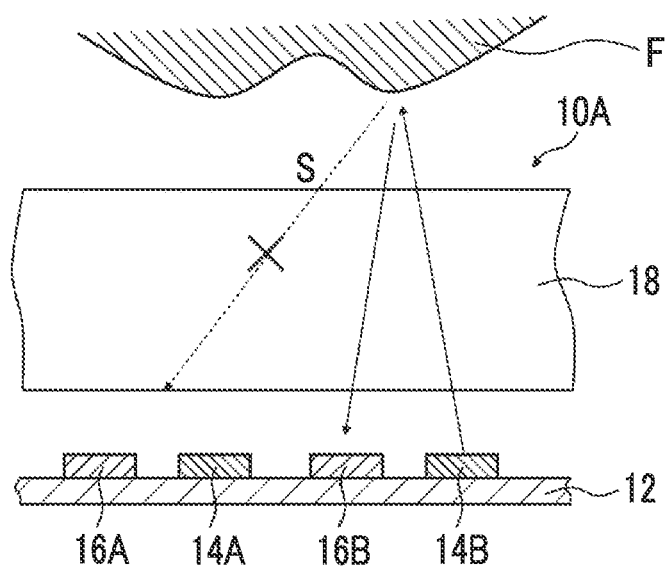
FIG. 10 is a schematic diagram illustrating a mechanism of absorbing stray light S to improve a S/N ratio in the second embodiment of the fingerprint recognition sensor according to the present invention.

Accordingly, as shown in FIG. 10, in the optical element 18, light that is incident from the second light emitting element 14B, is reflected from the finger F, and travels toward the second light-receiving element 16B is not absorbed, but the stray light S that is a part of the incident from the second light emitting element 14B and reflected from the finger F and travels toward the direction of the first light-receiving element 16A can be absorbed. As a result, the S/N ratio can be improved.

Hereinafter, each of the members will be described in detail.

[Light-Receiving Element]

The light-receiving element in the fingerprint recognition sensor according to the embodiment of the present invention is not particularly limited, and any light-receiving element can be preferably used as long as it is an element having a function of generating current or voltage due to a photovoltaic effect.

Examples of the above-described light-receiving element include an element in which a charge coupled device (CCD), a complementary metal-oxide semiconductor (CMOS), or the like is formed on a well-known semiconductor substrate such as a silicon substrate.

[Optical Element]

As described above, the optical element in the fingerprint recognition sensor according to the embodiment of the present invention is the specific optical element including the near infrared absorbing dichroic substance. The near infrared absorbing dichroic substance will be described in detail as a component of a composition described below.

In the present invention, the thickness of the optical element is not particularly limited and can be adjusted to be 10 μm or less such that the optical element can be formed using an application method as described below in a forming method without using a louver film.

From the viewpoint of thinning the fingerprint recognition sensor, the thickness of the optical element is preferably 0.5 to 8.0 μm and more preferably 0.5 to 6.0 μm.

In the present specification, the thickness of the optical element refers to the average thickness of the optical element. The average thickness is obtained by measuring the thicknesses of any five or more points of the optical element and obtaining an arithmetic mean value thereof.

In the present invention, from the viewpoint that absorption properties in the in-plane direction and absorption properties in the thickness direction can be adjusted independently, the above-described first embodiment is preferable, that is, it is preferable that the optical element includes: a first layer that includes a near infrared absorbing dichroic substance and has an absorption axis with respect to near infrared light in an in-plane direction; and a second layer that includes a near infrared absorbing dichroic substance and has an absorption axis with respect to near infrared light in a thickness direction.

In addition, it is preferable that the second layer does not have absorption anisotropy with respect to near infrared light in the in-plane direction. "Not having absorption anisotropy with respect to near infrared light in the in-plane direction" represents that, in a case where linearly polarized light of near infrared light is radiated from the normal direction of the optical element while changing the azimuthal angle to 360° at intervals of 5°, a difference between a maximum value and a minimum value of absorbance is within 5° from the maximum value.

In the first embodiment, in a case where a display element is laminated below the optical element, from the viewpoint of preventing interference of visible light from the display element, it is preferable that the first layer and the second layer are layers that do not substantially absorb visible light.

Here, "the layer that does not substantially absorb visible light" refers to a layer having a specific peak and a transmittance of 80% or more in a visible wavelength range of 400 nm or more and less than 700 nm in a case where the transmittance of the layer in the visible wavelength range is measured.

In the present invention, from the viewpoints of uniformly completing coating and easily realizing thinning, the above-described second embodiment is preferable, that is, it is preferable that the optical element consists of a single layer that includes a near infrared absorbing dichroic substance and has an absorption axis with respect to near infrared light in an in-plane direction, and in a cross-section taken along the absorption axis, the optical element does not have absorption anisotropy with respect to near infrared light.

Here, "not having absorption anisotropy with respect to near infrared light" represents that, in a case where an absorbance of the absorption axis with respect to near infrared light in the in-plane direction is represented by kx, in a case where an absorbance of an transmission axis with respect to near infrared light in the in-plane direction is represented by ky, and an absorbance in the thickness direction is represented by kz, the following relational expression is satisfied.

$$kx = kz > ky$$

In addition, regarding the state where "not having absorption anisotropy with respect to near infrared light", a cross-section taken along the transmission axis with respect to near infrared light in the in-plane direction is observed by transmission microscopy using a polarization microscope, and a state not having retardation can be evaluated as "not having absorption anisotropy with respect to near infrared light".

In the second embodiment, in a case where a display element is laminated below the optical element, from the viewpoint of preventing interference of visible light from the display element, it is preferable that the near infrared absorbing dichroic substance is a substance that does not substantially absorb visible light.

Here, "the substance that does not substantially absorb visible light" refers to a substance having a specific peak and a transmittance of 80% or more in a visible wavelength range of 400 nm or more and less than 700 nm in a case where the transmittance of the substance in the visible wavelength range is measured.

In the second embodiment, from the viewpoint of easily forming a negative A-Plate, it is preferable that the near infrared absorbing dichroic substance is a disk-like colorant.

The disk-like colorant will be described below in detail as a component of the composition described below.

From the viewpoint of adjusting the alignment state of the above-described near infrared absorbing dichroic substance, it is preferable that the layer configuration of the light emitting element is a layer that is formed of a composition including the above-described near infrared absorbing dichroic substance and a liquid crystal compound.

Hereinafter, the components in the composition will be described in detail, and then a method of forming the layer in the optical element will be described in detail.

<Liquid Crystal Compound>

The kind of the liquid crystal compound is not particularly limited and can be classified into a rod-like type (rod-like liquid crystal compound) and a disk-like type (disk-like liquid crystal compound or a discotic liquid crystal compound) in terms of the shape. Further, the liquid crystal compound can also be classified into a low molecular weight type and a polymer type. In general, the polymer refers to a compound having a polymerization degree of 100 or higher (Polymer Physics-Phase Transition Dynamics, Masao Doi, page 2, Iwanami Shoten Publishers, 1992). In addition, two or more rod-like liquid crystal compounds, two or more disk-like liquid crystal compounds, or a mixture of a rod-like liquid crystal compound and a disk-like liquid crystal compound may be used.

The position of the maximal absorption wavelength of the liquid crystal compound is not particularly limited and is preferably positioned in an ultraviolet range.

Since a change in temperature and a change in humidity of the optical characteristics can be reduced, a liquid crystal compound having a polymerizable group (a rod-like liquid crystal compound or a disk-like liquid crystal compound) is preferable as the liquid crystal compound. The liquid crystal compound may also be a mixture of two or more kinds. In this case, it is preferable that at least one liquid crystal compound has two or more polymerizable groups.

That is, it is preferable that the optically-anisotropic layer is formed by immobilizing a liquid crystal compound having a polymerizable group (a rod-like liquid crystal compound or a disk-like liquid crystal compound) by polymerization or the like. In this case, it is not necessary that the layer formed of the liquid crystal compound exhibits liquid crystal properties.

The kind of the above-described polymerizable group is not particularly limited, and a polymerizable group capable of radical polymerization or cationic polymerization is preferable.

As the radically polymerizable group, a well-known radically polymerizable group can be used, and an acryloyl group or a methacryloyl group is preferable.

As the cationically polymerizable group, a well-known cationically polymerizable group can be used, and specific examples thereof include an alicyclic ether group, a cyclic acetal group, a cyclic lactone group, a cyclic thioether group, a spiro ortho ester group, and a vinyloxy group. In particular, an alicyclic ether group or a vinyloxy group is preferable, and an epoxy group, an oxetanyl group, or a vinyloxy group is more preferable.

In particular, preferable examples of the polymerizable group are as follows.

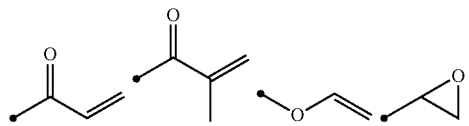

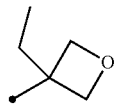

As the liquid crystal compound, a compound represented by Formula (I) is preferable.

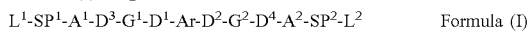

$L^1\text{-}SP^1\text{-}A^1\text{-}D^3\text{-}G^1\text{-}D^1\text{-}Ar\text{-}D^2\text{-}G^2\text{-}D^4\text{-}A^2\text{-}SP^2\text{-}L^2$      Formula (I)

In Formula (I), $D^1$, $D^2$, $D^3$, and $D^4$ each independently represent a single bond, —O—CO—, —C(=S)O—, —$CR^1R^2$—, —$CR^1R^2$—$CR^3R^4$—, —O—$CR^1R^2$—, —$CR^1R^2$—O—$CR^3R^4$—, —CO—O—$CR^1R^2$—, —O—CO—$CR^1R^2$—, —$CR^1R^2$—O—CO—$CR^3R^4$—, —$CR^1R^2$—CO—O—$CR^3R^4$—, —$NR^1$—$CR^2R^3$—, or —CO—$NR^1$—.

$R^1$, $R^2$, $R^3$, and $R^4$ each independently represent a hydrogen atom, a fluorine atom, or an alkyl group having 1 to 4 carbon atoms.

In addition, in Formula (I), $G^1$ and $G^2$ each independently represent a divalent alicyclic hydrocarbon group having 5 to 8 carbon atoms, and one or more —$CH_2$—'s forming the alicyclic hydrocarbon group may be substituted with —O—, —S—, or —NH—.

In addition, in Formula (I), $A^1$ and $A^2$ each independently represent a single bond, an aromatic ring having 6 or more carbon atoms, or a cycloalkylene ring having 6 or more carbon atoms.

In addition, in Formula (I), $SP^1$ and $SP^2$ each independently represent a single bond, a linear or branched alkylene group having 1 to 14 carbon atoms, or a divalent linking group in which one or more —$CH_2$—'s forming the linear or branched alkylene group having 1 to 14 carbon atoms are substituted with —O—, —S—, —NH—, —N(Q)-, or —CO—, and Q represents a polymerizable group.

In addition, in Formula (I), $L^1$ and $L^2$ each independently a monovalent organic group (for example, an alkyl group or a polymerizable group).

In a case where Ar represents a group represented by Formula (Ar-1), Formula (Ar-2), Formula (Ar-4), or Formula (Ar-5) described below, at least one of $L^1$ or $L^2$ represents a polymerizable group. In addition, in a case where Ar represents a group represented by Formula (Ar-3) described below, at least one of $L^1$ and $L^2$ and $L^3$ and $L^4$ in Formula (Ar-3) described below represents a polymerizable group.

As the divalent alicyclic hydrocarbon group having 5 to 8 carbon atoms represented by $G^1$ and $G^2$ in Formula (I), a 5- or 6-membered ring is preferable. In addition, the alicyclic hydrocarbon group may be a saturated alicyclic hydrocarbon group or an unsaturated alicyclic hydrocarbon group and is preferably a saturated alicyclic hydrocarbon group. The details of the divalent alicyclic hydrocarbon group represented by $G^1$ and $G^2$ can be found in, for example, paragraph "0078" of JP2012-21068A, the content of which is incorporated herein by reference.

Examples of the aromatic ring having 6 or more carbon atoms represented by $A^1$ and $A^2$ in Formula (I) include: an aromatic hydrocarbon ring such as a benzene ring, a naphthalene ring, an anthracene ring, or a phenanthroline ring; and an aromatic heterocyclic ring such as a furan ring, a pyrrole ring, a thiophene ring, a pyridine ring, a thiazole ring, or a benzothiazole ring. In particular, a benzene ring (for example, a 1,4-phenyl group) is preferable.

Furthermore, examples of the cycloalkylene ring having 6 or more carbon atoms represented by each of $A^1$ and $A^2$ in Formula (I) include a cyclohexane ring and a cyclohexene ring. Among these, a cyclohexane ring (for example, a cyclohexane-1,4-diyl group) is preferable.

In Formula (I), as the linear or branched alkylene group having 1 to 14 carbon atoms represented by each of $SP^1$ and $SP^2$, a methylene group, an ethylene group, a propylene group, or a butylene group is preferable.

The polymerizable group represented by $L^1$ and $L^2$ in Formula (I) is not particularly limited, and a radically polymerizable group (a group capable of radical polymerization) or a cationically polymerizable group (a group capable of cationic polymerization) is preferable.

A preferable range of the radically polymerizable group is as described above.

On the other hand, in Formula (I), Ar represents any aromatic ring selected from the group consisting of groups represented by the following Formulae (Ar-1) to (Ar-5). In the following Formulae (Ar-1) to (Ar-5), *1 represents a bonding position to $D^1$, and *2 represents a bonding position to $D^2$.

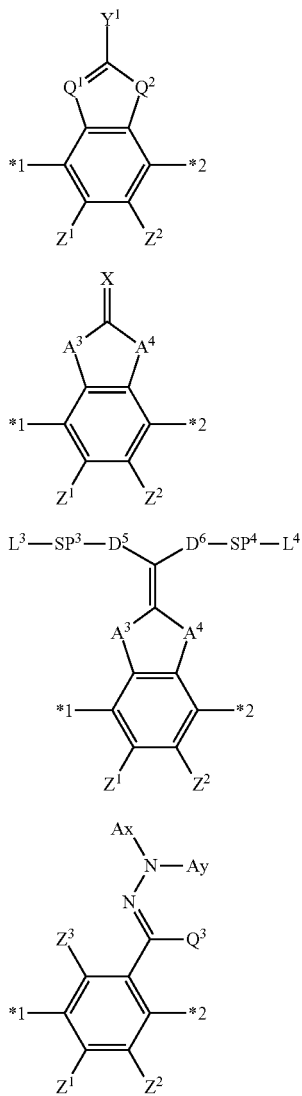

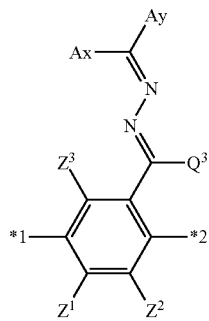

Here, in Formula (Ar-1), $Q^1$ represents N or CH, $Q^2$ represents —S—, —O—, or —N($R^5$)—, $R^5$ represents a hydrogen atom or an alkyl group having 1 to 6 carbon atoms, and $Y^1$ represents an aromatic hydrocarbon group having 6 to 12 carbon atoms or an aromatic heterocyclic group having 3 to 12 carbon atoms each of which may have a substituent.

Examples of the alkyl group having 1 to 6 carbon atoms represented by $R^5$ include a methyl group, an ethyl group, a propyl group, an isopropyl group, an n-butyl group, an isobutyl group, a sec-butyl group, a tert-butyl group, an n-pentyl group, and an n-hexyl group.

Examples of the aromatic hydrocarbon group having 6 to 12 carbon atoms represented by $Y^1$ include a phenyl group, a 2,6-diethylphenyl group, and an aryl group such as a naphthyl group.

Examples of the aromatic heterocyclic group having 3 to 12 carbon atoms represented by $Y^1$ include a thienyl group, a thiazolyl group, a furyl group, a pyridyl group, and a heteroaryl group such as a benzofuryl group. The aromatic heterocyclic group include a group in which a benzene ring and an aromatic heterocyclic ring are fused.

In addition, examples of the substituent which may be included in $Y^1$ include an alkyl group, an alkoxy group, a nitro group, an alkylsulfonyl group, an alkyloxycarbonyl group, a cyano group, and a halogen atom.

As the alkyl group, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a t-butyl group, or a cyclohexyl group) is more preferable, an alkyl group having 1 to 4 carbon atoms is still more preferable, and a methyl group or an ethyl group is still more preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, or a methoxyethoxy group) is more preferable, an alkoxy group having 1 to 4 carbon atoms is still more preferable, and a methoxy group or an ethoxy group is still more preferable.

Examples of the halogen atom include a fluorine atom, a chlorine atom, a bromine atom, and an iodine atom. Among these, a fluorine atom or a chlorine atom is preferable.

In addition, in Formulae (Ar-1) to (Ar-5), $Z^1$, $Z^2$, and $Z^3$ each independently represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$NR^6R^7$, or —$SR^8$, $R^6$ to $R^8$ each independently represent a hydrogen atom or an alkyl group having 1 to 6 carbon atoms, and $Z^1$ and $Z^2$ may be bonded to each other to form a ring. The ring may be any one of an alicyclic ring, a heterocyclic ring, or an aromatic ring and is preferably an aromatic ring. The formed ring may be substituted with a substituent.

As the monovalent aliphatic hydrocarbon group having 1 to 20 carbon atoms, an alkyl group having 1 to 15 carbon atoms is preferable, an alkyl group having 1 to 8 carbon atoms is more preferable, a methyl group, an ethyl group, an isopropyl group, a tert-pentyl group (1,1-dimethylpropyl group), a tert-butyl group, or a 1,1-dimethyl-3,3-dimethylbutyl group is still more preferable, and a methyl group, an ethyl group, or a tert-butyl group is still more preferable.

Examples of the monovalent alicyclic hydrocarbon group having 3 to 20 carbon atoms include: a monocyclic saturated hydrocarbon group such as a cyclopropyl group, a cyclobutyl group, a cyclopentyl group, a cyclohexyl group, a cycloheptyl group, a cyclooctyl group, a cyclodecyl group, a methylcyclohexyl group, or an ethylcyclohexyl group; a monocyclic unsaturated hydrocarbon group such as a cyclobutenyl group, a cyclopentenyl group, a cyclohexenyl group, a cycloheptenyl group, a cyclooctenyl group, a cyclodecenyl group, a cyclopentadienyl group, a cyclohexadienyl group, a cyclooctadienyl group, or a cyclodecadiene group; and a polycyclic saturated hydrocarbon group such as a bicyclo[2.2.1]heptyl group, a bicyclo[2.2.2]octyl group, a tricyclo[5.2.1.0$^{2,6}$]decyl group, a tricyclo[3.3.1.1$^{3,7}$]decyl group, a tetracyclo[6.2.1.1$^{3,6}$.0$^{2,7}$]dodecyl group, or an adamantyl group.

Examples of the monovalent aromatic hydrocarbon group having 6 to 20 carbon atoms include a phenyl group, a 2,6-diethylphenyl group, a naphthyl group, and a biphenyl group. In particular, an aryl group (in particular, a phenyl group) having 6 to 12 carbon atoms is preferable.

Examples of the halogen atom include a fluorine atom, a chlorine atom, a bromine atom, and an iodine atom. Among these, a fluorine atom, a chlorine atom, or a bromine atom is preferable.

On the other hand, examples of the alkyl group having 1 to 6 carbon atoms represented by $R^6$ to $R^8$ include a methyl group, an ethyl group, a propyl group, an isopropyl group, an n-butyl group, an isobutyl group, a sec-butyl group, a tert-butyl group, an n-pentyl group, and an n-hexyl group.

In addition, in Formulae (Ar-2) and (Ar-3), $A^3$ and $A^4$ each independently represent a group selected from the group consisting of —O—, —N($R^9$)—, —S—, and —CO—, and $R^9$ represents a hydrogen atom or a substituent.

Examples of the substituent represented by $R^9$ are the same as those of the substituent which may be included in $Y^1$ in Formula (Ar-1).

In addition, in Formula (Ar-2), X represents a non-metal atom in Group 14 to Group 16 which may be bonded to a hydrogen atom or a substituent.

In addition, examples of the non-metal atom in Group 14 to Group 16 represented by X include an oxygen atom, a sulfur atom, a nitrogen atom having a substituent, and a carbon atom having a substituent. Examples of the substituent are the same as those of the substituent which may be included in $Y^1$ in Formula (Ar-1).

In addition, in Formula (Ar-3), $D^5$ and $D^6$ each independently represent a single bond, —O—CO—, —C(=S)O—, —CR$^1$R$^2$—, —CR$^1$R$^2$—CR$^3$R$^4$—, —O—CR$^1$R$^2$—, —CR$^1$R$^2$—O—CR$^3$R$^4$—, —CO—O—CR$^1$R$^2$—, —O—CO—CR$^1$R$^2$—, —CR$^1$R$^2$—O—CO—CR$^3$R$^4$—, —CR$^1$R$^2$—CO—O—CR$^3$R$^4$—, —NR$^1$—CR$^2$R$^3$—, or —CO—NR$^1$—. $R^1$, $R^2$, $R^3$, and $R^4$ each independently represent a hydrogen atom, a fluorine atom, or an alkyl group having 1 to 4 carbon atoms.

In addition, in Formula (Ar-3), SP$^3$ and SP$^4$ each independently represent a single bond, a linear or branched alkylene group having 1 to 12 carbon atoms, or a divalent linking group in which one or more —CH$_2$—'s forming the linear or branched alkylene group having 1 to 12 carbon atoms are substituted with —O—, —S—, —NH—, —N(Q)-, or —CO—, and Q represents a polymerizable group.

Furthermore, in Formula (Ar-3), $L^3$ and $L^4$ each independently represent a monovalent organic group (for example, an alkyl group and a polymerizable group), and at least one of $L^3$ or $L^4$, or $L^1$ or $L^2$ in Formula (I) represents a polymerizable group.

In addition, in Formulae (Ar-4) and (Ar-5), Ax represents an organic group having 2 to carbon atoms that has at least one aromatic ring selected from the group consisting of an aromatic hydrocarbon ring and an aromatic heterocyclic ring.

In addition, in Formulae (Ar-4) and (Ar-5), Ay represents a hydrogen atom, an alkyl group having 1 to 6 carbon atoms which may have a substituent, or an organic group having 2 to 30 carbon atoms that has at least one aromatic ring selected from the group consisting of an aromatic hydrocarbon ring and an aromatic heterocyclic ring.

Here, the aromatic ring represented by Ax and Ay may have a substituent, and Ax and Ay may be bonded to each other to form a ring.

In addition, $Q^3$ represents a hydrogen atom or an alkyl group having 1 to 6 carbon atoms which may have a substituent.

Examples of Ax and Ay are described in paragraphs "0039" to "0095" of WO2014/010325A.

Examples of the alkyl group having 1 to 6 carbon atoms represented by $Q^3$ include a methyl group, an ethyl group, a propyl group, an isopropyl group, an n-butyl group, an isobutyl group, a sec-butyl group, a tert-butyl group, an n-pentyl group, and an n-hexyl group. Examples of the substituent are the same as those of the substituent which may be included in $Y^1$ in Formula (Ar-1).

From the viewpoint of further improving the effects of the present invention, it is preferable that at least one of $A^1$ or $A^2$ represents a cycloalkylene ring having 6 or more carbon atoms, and it is more preferable that one of $A^1$ or $A^2$ represents a cycloalkylene ring having 6 or more carbon atoms.

In addition, as the liquid crystal compound, a disk-like liquid crystal compound (discotic liquid crystal molecule) described below in detail can be used.

In general, the discotic liquid crystal molecule has a disk-like partial structure in a mother nucleus thereof.

The disk-like structure in the mother nucleus portion excluding side chain portions can be defined by lengths a, b, and c obtained from the following (1) to (4) or the following (1), (2), and (3') to (5').

(1) Regarding the disk-like structure of the discotic liquid crystal molecule, a molecular structure that is as close to a plane as possible is constructed. As a bond distance and a bond angle, standard values corresponding to orbital hybridization are preferably used. The standard values are described in "Handbook of Chemistry", revised fourth edition, Basic II, Chapter 15 (published by MARUZEN in 1993), edited by The Chemical Society of Japan.

(2) The structure obtained in (1) as an initial value is optimized using a molecular orbital method or a molecular force field method. As the optimization method, Gaussian92, MOPAC93, CHARMm/QUANTA, or MM3 can be applied. In particular, Gausian92 is preferable.

(3) Each of atoms in the optimized disk-like structure is assigned with a sphere defined by van der Waals radius to describe the shape of the molecule.

(4) Three edges of a minimum cuboid where the disk-like structure having the shape obtained in (3) are set to a, b, and c.

In order to reduce arbitrariness, it is preferable to perform the following (3') to (5') instead of (3) and (4).

(3') The centroid of the structure obtained by the structure optimization is moved to an origin, and coordinate axes are set to principal axes of inertia (principal axes of inertia tensor ellipsoid).

(4') Each of the atoms is assigned with a sphere defined by van der Waals radius to describe the shape of the molecule.

(5') Lengths of coordinate axis directions on the van der Waals surface are measured and set to a, b, and c, respectively.

In a case where the disk-like structure is defined by the a, b, and c obtained through the above-described procedure, it is preferable that the disk-like structure satisfies a relationship of a≥b>c and a≥b≥a/2. It is more preferable that the disk-like structure satisfies a relationship of a≥b>c and a≥b≥0.7a. In addition, it is preferable that b/2>c is satisfied.

As the discotic liquid crystal molecule, various known compounds are proposed (described in, for example, a research report by C. Destrade et al., Mol. Cryst. Liq. Cryst., vol. 71, p. 111 (1981); "Science of Liquid Crystal", edited by the Chemical Society of Japan, Seasonal Chemical Review No. 22, Chapter 5, and Chapter 10, Section 2 (1994); a research report by B. Kohne et al., Angew. Chem. Vol. 96, p. 70 (1984); a research report by J. M. Lehn et al., J. Chem. Soc. Chem. Commun., p. 1794 (1985); or a research report by J. Zhang and J. S. Moore et al., J. Am. Chem. Soc., vol. 116, p. 2655 (1994). Examples of the disk-like structure in the center portion include a benzene ring, a cyclohexane ring, a triphenylene ring, a truxene ring, a coronene ring, a phthalocyanine ring, a porphyrin ring, an aza crown ring, an acetylene-macrocycle ring, and a β-diketone-based metal complex ring. Examples of the disk-like structure are also described in "Chemical Review No. 15, Chemistry of Novel Aromatic Series" edited by the Chemical Society of Japan (published by University of Tokyo Press in 1977). In addition, as in the metal complex, an aggregate of a plurality of molecules may be formed by a hydrogen bond or a coordinate bond to form the disk-like structure.

The discotic liquid crystal molecule is a compound having a structure a plurality of side chain portions that are the same as or different from each other extend in a radial shape from the disk-like structure in the center portion. Examples of the side chain portion include an alkanoyloxy group, an alkylsulfonyl group, an alkylthio group, an alkoxy group, a 2-(4-alkylphenyl)ethynyl group, a terminal vinyl alkoxy group, a 4-alkoxyphenyl group, an alkoxymethyl group, an alkylthiomethyl group, a 2-alkylthioethoxymethyl group, a 2-alkoxyethoxymethyl group, a 2-alkoxycarbonylethyl group, cholesteryl oxycarbonyl, a 4-alkoxyphenoxycarbonyl group, a 4-alkoxybenzoyloxy group, a 4-alkylbenzoyloxy group, a 4-alkoxybenzoyl group, a 4-alkoxycinnamoyloxy group, a 4-alkylcinnamoyloxy group, and a 4-alkoxycinnamoyl group.

Examples of the alkanoyloxy group include hexanoyloxy, heptanoyloxy, octanoyloxy, nonanoyloxy, decanoyloxy, and undecanoyloxy. Examples of the alkylsulfonyl group include hexylsulfonyl, heptylsulfonyl, octylsulfonyl, nonylsulfonyl, decylsulfonyl, and undecylsulfonyl. Examples of the alkylthio group include hexylthio, heptylthio, octylthio, nonylthio, decylthio, undecylthio, and dodecylthio. Examples of the alkoxy group include butoxy, pentyloxy, hexyloxy, heptyloxy, octyloxy, nonyloxy, decyloxy, and undecyloxy. Examples of the 2-(4-alkylphenyl)ethynyl group include 2-(4-methylphenyl)ethynyl, 2-(4-ethylphenyl)ethynyl, 2-(4-propylphenyl)ethynyl, 2-(4-butylphenyl)ethynyl, 2-(4-pentylphenyl)ethynyl, 2-(4-hexylphenyl)ethynyl, 2-(4-heptylphenyl)ethynyl, 2-(4-octylphenyl)ethynyl, and 2-(4-nonylphenyl)ethynyl. Examples of the terminal vinyl alkoxy group include 4-vinylbutoxy, 5-vinylpentyloxy, 6-vinylhexyloxy, 7-vinylheptyloxy, 8-vinyloctyloxy, and 9-vinylnonyloxy.

Examples of the alkoxy portion in the 4-alkoxyphenyl group are the same as the examples of the alkoxy group. Examples of the alkoxy portion in the alkoxymethyl group are the same as the examples of the alkoxy group. Examples of the alkylthio portion in the alkylthiomethyl group are the same as the examples of the alkylthio group. Examples of the alkylthio portion in the 2-alkylthioethoxymethyl group are the same as the examples of the alkylthio group. Examples of the alkoxy portion in the 2-alkoxycarbonylethyl group are the same as the examples of the alkoxy group. Examples of the alkoxy portion in the 4-alkoxyphenoxycarbonyl group are the same as the examples of the alkoxy group. Examples of the alkoxy portion in the 4-alkoxybenzoyloxy group are the same as the examples of the alkoxy group. Examples of the 4-alkylbenzoyloxy group include 4-methylbenzoyloxy, 4-ethylbenzoyloxy, 4-propylbenzoyloxy, 4-butylbenzoyloxy, 4-pentylbenzoyloxy, 4-hexylbenzoyloxy, 4-heptylbenzoyloxy, 4-octylbenzoyloxy, and 4-nonylbenzoyloxy. Examples of the alkoxy portion in the 4-alkoxybenzoyl group are the same as the examples of the alkoxy group.

Examples of the alkoxy portion in the 4-alkoxycinnamoyloxy group are the same as the examples of the alkoxy group. Examples of the 4-alkylcinnamoyloxy group include 4-methylcinnamoyloxy, 4-ethylcinnamoyloxy, 4-propylcinnamoyloxy, 4-butylcinnamoyloxy, 4-pentylcinnamoyloxy, 4-hexylcinnamoyloxy, 4-heptylcinnamoyloxy, 4-octylcinnamoyloxy, and 4-nonylcinnamoyloxy. Examples of the alkoxy portion in the 4-alkoxycinnamoyl group are the same as the examples of the alkoxy group. In the side chain portion, the phenyl portion in each of the examples may be replaced with another aryl group (for example, naphthyl, phenanthryl, or anthracenyl). Each of the examples may further have a substituent. In addition, each of the examples may further have a substituent in addition to the above-described substituent. In addition, in the side chain portion, the phenyl portion in each of the examples may be replaced with an aromatic heterocyclic group (for example, pyridyl, pyrimidyl, triazinyl, thienyl, furyl, pyrrolyl, pyrazolyl, imidazolyl, triazolyl, thiazolyl, oxazolyl, thiadiazolyl, oxadiazolyl, quinolyl, or isoquinolyl).

Examples of the discotic liquid crystal molecule consisting of an organic metal complex include an organic silicon-based metal complex such as diisobutylsilanediol (Eaborn et al., J. Chem. Soc., page 549, 1955), a β-diketone-based metal complex (Ota et al., J. Chem. Soc., Commun., page 1099, 1984), a long-chain-substituted phthalocyanine-based metal complex (Simon et al., J. Amer. Chem. Soc., vol. 104, page 5244, 1982), a dithiolene-based metal complex (Ota et al., J. Chem. Soc., Chem. Commun., page 883, 1986), a porphyrin-based metal complex (Shimizu et al., Chem. Lett., page 1041, 1986), a metal (II) carboxylate-based binuclear complex (Giroud et al., J. Phys. Lett., vol. 45, page L-681, 1984), an imine-based Pd binuclear complex (Simon et al., Liq. Cryst., vol. 4, page 707, 1989), and a bis(glyoxymato) metal (II)-based complex (Ota et al., Mol. Cryst. Liq. Cryst., vol. 203. page 43, 1991). Using novel physical properties that the liquid crystal in the related art does not have, the organic metal complex-based liquid crystal may be applicable to new uses, for example, (1) the use of discoloration such as thermochromism or electrochromism, (2) the application to dye liquid crystal using rich coloration of the complex, (3) the application of an one-dimensional conductor, and (4) the application to a ferromagnetic substance.

The discotic liquid crystal phase is classified into a discotic nematic phase and a columnar phase, and the columnar phase is further classified into a hexagonal phase, a rectangular phase, and a tetragonal phase (described in a research report by H. Zimmerman et al., Israel Journal of Chemistry, vol. 23, page 341 (1983)). Recently, a discotic lamellar phase or a chiral discotic nematic phase is also further reported. In the present invention, it is preferable that the discotic liquid crystal molecule forms the discotic nematic (ND) phase.

In addition, it is preferable that the disk-like liquid crystal compound is a compound represented by the following Formula (D).

D(-L-Q)$n$               Formula (D)

In the formula, D represents a disk-like core, L represents a divalent linking group, and Q represents a polymerizable group. In addition, n represents an integer of 3 to 12. Examples of the disk-like core (D) of the formula are shown below. In each of the following examples, LQ (or QL) represents a combination of the divalent linking group (L) and the polymerizable group (Q). Structural formulae of specific examples (D1 to D16) of Formula (D) are shown below.

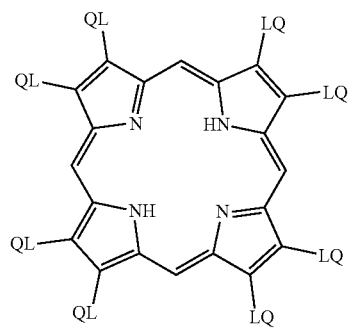

(D1)

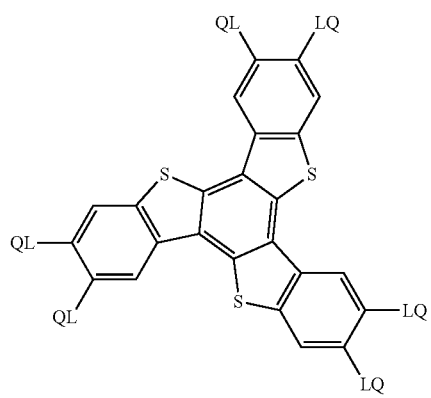

(D2)

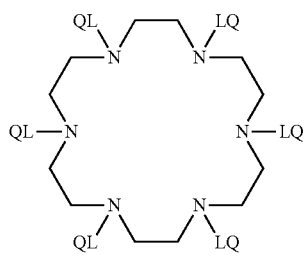

(D3)

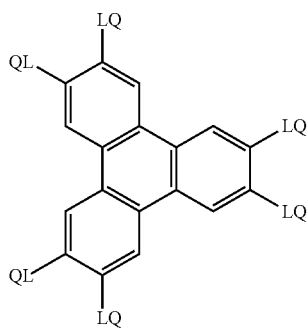

(D4)

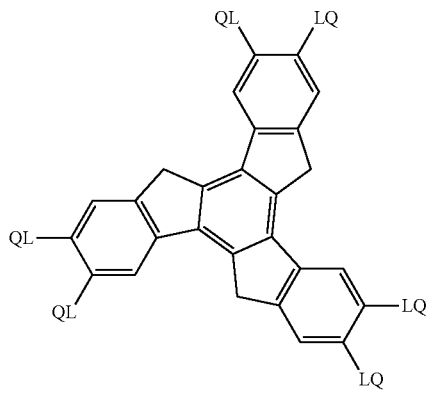

(D5)

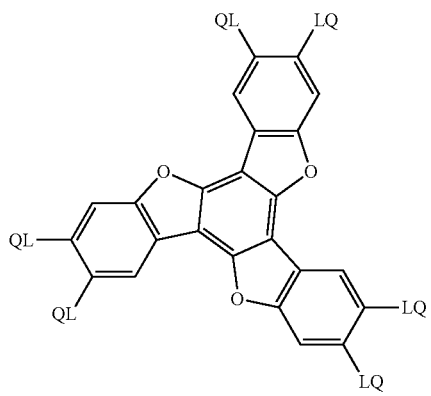

(D6)

(D7) 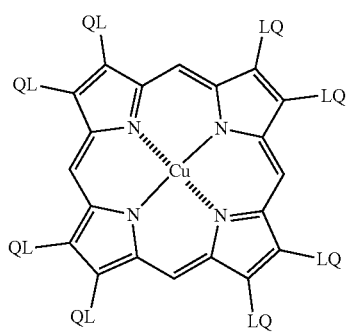
(D8) 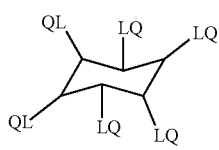
(D9) 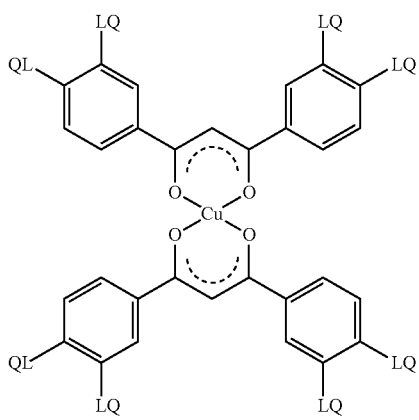
(D10) 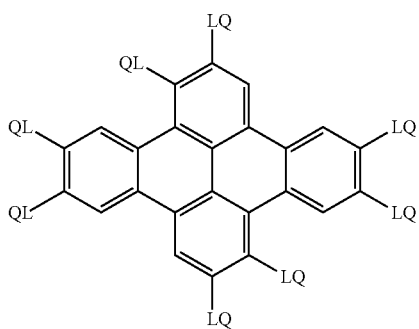
(D11) 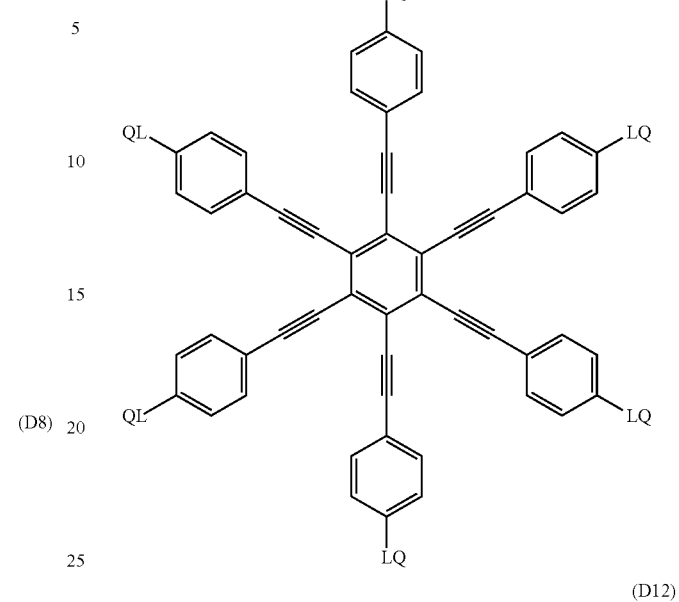
(D12) 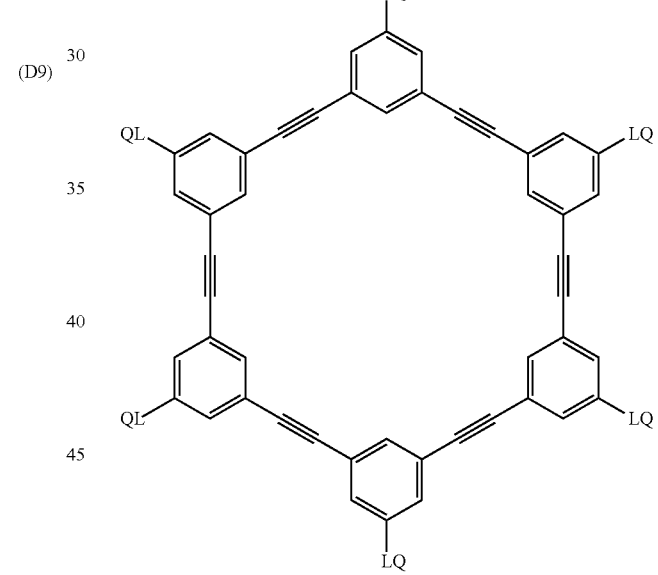
(D13) 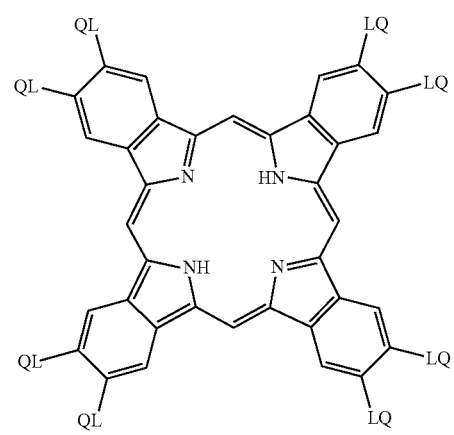

-continued (D14)
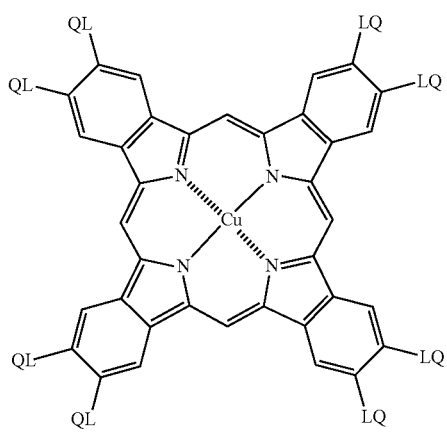

(D15)
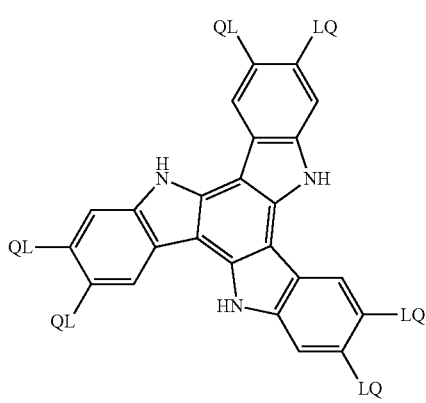

(D16)
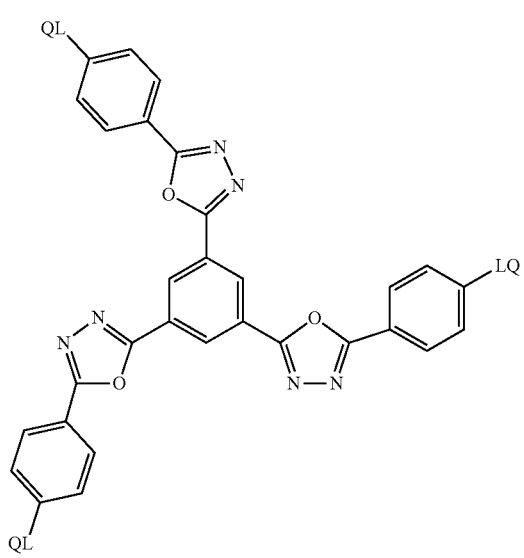

It is preferable that L in Formula (D) represents a divalent linking group selected from the group consisting of an alkylene group, an alkenylene group, an arylene group, —C(=O)—, —NH—, —O—, —S—, and a combination thereof. It is more preferable that L represents a group obtained by combing at least two divalent groups selected from the group consisting of an alkylene group, an alkenylene group, an arylene group, —C(=O)—, —NH—, —O—, and —S—. It is most preferable that L represents a group obtained by combing at least two divalent groups selected from the group consisting of an alkylene group, an alkenylene group, an arylene group, —C(=O)—, and —O—. The number of carbon atoms in the alkylene group is preferably 1 to 12. The number of carbon atoms in the alkenylene group is preferably 2 to 12. The number of carbon atoms in the arylene group is preferably 6 to 10. The alkylene group, the alkenylene group, and the arylene group may have a substituent (for example, an alkyl group, a halogen atom, a cyano group, an alkoxy group, and an acyloxy group).

Examples of the divalent linking group (L) are shown below. In each of the formulae, the left side is bonded to the disk-like core (D), and the right side is bonded to the polymerizable group (Q). AL represents an alkylene group or an alkenylene group, and AR represents an arylene group.

L1: -AL-C(=O)—O-AL-
L2: -AL-C(=O)—O-AL-O—
L3: -AL-C(=O)—O-AL-O-AL-
L4: -AL-C(=O)—O-AL-O—C(=O)—
L5: —C(=O)-AR—O-AL-
L6: —C(=O)-AR—O-AL-O—
L7: —C(=O)-AR—O-AL-O—C(=O)—
L8: —C(=O)—NH-AL-
L9: —NH-AL-O—
L10: —NH-AL-O—C(=O)—
L11: —O-AL-
L12: —O-AL-O—
L13: —O-AL-O—C(=O)—
L14: —O-AL-O—C(=O)—NH-AL-
L15: —O-AL-S-AL-
L16: —O—C(=O)-AL-AR—O-AL-O—C(=O)—
L17: —O—C(=O)-AR—O-AL-C(=O)—
L18: —O—C(=O)-AR—O-AL-O—C(=O)—
L19: —O—C(=O)-AR—O-AL-O-AL-O—C(=O)—
L20: —O—C(=O)-AR—O-AL-O-AL-O-AL-O—C(=O)—
L21: —S-AL-
L22: —S-AL-O—
L23: —S-AL-O—C(=O)—
L24: —S-AL-S-AL-
L25: —S-AR-AL-

The polymerizable group (Q) in Formula (D) is not particularly limited and can be determined depending on the kind of the polymerization reaction. Examples of the polymerizable group are the same as the examples of Q in Formula (III) described below.

In Formula (D) n represents an integer of 3 to 12. A specific number is determined depending on the kind of the disk-like core (D). n represents preferably an integer of 3 to 6 and most preferably 3. Combinations of a plurality of L's and a plurality of Q's may be different from each other but are preferably the same as each other.

As the compound having a disk shape, two or more kinds of discotic liquid crystal compounds may be used in combination. For example, a molecule having the polymerizable group (Q) and a molecule not having the polymerizable group (Q) may be used in combination.

It is preferable that the non-polymerizable discotic liquid crystal compound is a compound having a hydrogen atom or an alkyl group instead of the polymerizable group (Q) of the polymerizable discotic liquid crystal compound. That is, it is preferable that the non-polymerizable discotic liquid crystal compound is a compound represented by the following formula.

In the formula, D represents a disk-like core, L represents a divalent linking group, and R represents a hydrogen atom or an alkyl group. In addition, n represents an integer of 3 to 12. Examples of the disk-like core (D) in the formula are the same as the examples of the polymerizable discotic liquid crystal compound, except that LQ (or QL) is changed to LR (or RL). In addition, examples of the divalent linking group (L) are the same as the examples of the polymerizable discotic liquid crystal compound. The alkyl group in R has preferably 1 to 40 carbon atoms and more preferably 1 to 30 carbon atoms. A chained alkyl group is preferable to a cyclic alkyl group, and a linear alkyl group is preferable to a branched chained alkyl group. It is still more preferable that R represents a hydrogen atom or a linear alkyl group having 1 to 30 carbon atoms.

In addition, it is more preferable that the disk-like liquid crystal compound is a compound represented by the following Formula (D-2).

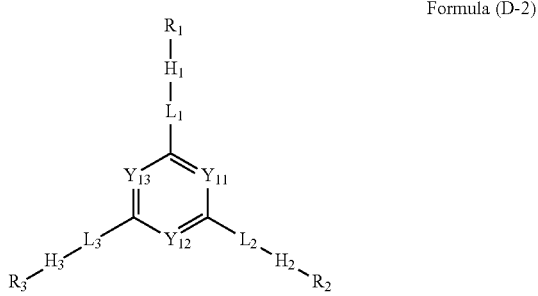

Formula (D-2)

In Formula (D-2), $Y_{11}$, $Y_{12}$, and $Y_{13}$ each independently represent methine or a nitrogen atom.

In a case where $Y_{11}$, $Y_{12}$, and $Y_{13}$ represent methine, the methine may have a substituent. Examples of the substituent include an alkyl group (for example, a methyl group, an ethyl group, an isopropyl group, or a tert-butyl group), an alkenyl group (for example, a vinyl group, an allyl group, a 2-butenyl group, or a 3-pentenyl group), an alkynyl group (for example, a propargyl group or a 3-pentynyl group), an aryl group (for example, a phenyl group, a p-methylphenyl group, or a naphthyl group), a substituted or unsubstituted amino group (for example, an unsubstituted amino group, a methylamino group, a dimethylamino group, a diethylamino group, or an anilino group), an alkoxy group (for example, a methoxy group, an ethoxy group, or a butoxy group), an aryloxy group (for example, a phenyloxy group or a 2-naphthyloxy group), an acyl group (for example, an acetyl group, a benzoyl group, a formyl group, or a pivaloyl group), an alkoxycarbonyl group (for example, a methoxycarbonyl group or an ethoxycarbonyl group), an aryloxycarbonyl group (for example, a phenyloxycarbonyl group), an acyloxy group (for example, an acetoxy group or a benzoyloxy group), an acylamino group (for example, an acetylamino group or a benzoylamino group), an alkoxycarbonylamino group (for example, a methoxycarbonylamino group), an aryloxycarbonylamino group (for example, a phenyloxycarbonylamino group), an alkylsulfonylamino group (for example, a methanesulfonylamino group), an arylsulfonylamino group (for example, a benzenesulfonylamino group), a sulfamoyl group (for example, a sulfamoyl group, an N-methylsulfamoyl group, an N,N-dimethylsulfamoyl group, or an N-phenylsulfamoyl group), a carbamoyl group (for example, an unsubstituted carbamoyl group, an N-methylcarbamoyl group, an N,N-diethylcarbamoyl group, or an N-phenylcarbamoyl group), an alkylthio group (for example, a methylthio group or an ethylthio group), an arylthio group (for example, a phenylthio group), an alkylsulfonyl group (for example, a mesyl group), an arylsulfonyl group (for example, a tosyl group), an alkylsulfinyl group (for example, a methanesulfinyl group), an arylsulfinyl group (for example, a benzenesulfinyl group), a ureido group (for example, an unsubstituted ureido group, a 3-methylureido group, or a 3-phenylureido group), a phosphoric amide group (for example, a diethyl phosphoric amide group or a phenyl phosphoric amide group), a hydroxyl group, a mercapto group, a halogen atom (for example, a fluorine atom, a chlorine atom, a bromine atom, or an iodine atom), a cyano group, a sulfo group, a carboxyl group, a nitro group, a hydroxamic acid group, a sulfino group, a hydrazino group, an imino group, a heterocyclic group (a heterocyclic group having a heteroatom such as a nitrogen atom, an oxygen atom, or a sulfur atom, and examples of the heterocyclic group having a heteroatom include an imidazolyl group, a pyridyl group, a quinolyl group, a furyl group, a piperidyl group, a morpholino group, a benzoxazolyl group, a benzimidazolyl group, and a benzothiazolyl group), and a silyl group (for example, a trimethylsilyl group or a triphenylsilyl group). The substituents may be further substituted with the substituents.

Among these, as the substituent of the methine, an alkyl group, an alkoxy group, an aryloxy group, an acyl group, an alkoxycarbonyl group, an acyloxy group, an acylamino group, an alkoxycarbonylamino group, an alkylthio group, an arylthio group, a halogen atom, or a cyano group is preferable, an alkyl group, an alkoxy group, an alkoxycarbonyl group, an acyloxy group, a halogen atom, or a cyano group is more preferable, and an alkyl group having 1 to 12 carbon atoms, an alkoxy group having 1 to 12 carbon atoms, an alkoxycarbonyl group having 2 to 12 carbon atoms, an acyloxy group having 2 to 12 carbon atoms, a halogen atom, or a cyano group is most preferable.

It is most preferable that $Y_{11}$, $Y_{12}$, and $Y_{13}$ represent methine, and it is most preferable that the methine is unsubstituted.

In Formula (D-2), $L_1$, $L_2$, and $L_3$ each independently represent a single bond or a divalent linking group. In a case where $L_1$, $L_2$, and $L_3$ represent a divalent linking group, it is preferable that $L_1$, $L_2$, and $L_3$ each independently represent a divalent linking group selected from the group consisting of —O—, —S—, —C(=O)—, —CH=CH—, —C≡C—, a divalent cyclic group, and a combination thereof. $R_7$ represents an alkyl group having 1 to 7 carbon atoms or a hydrogen atom, preferably an alkyl group having 1 to 4 carbon atoms or a hydrogen atom, and more preferably a methyl group, an ethyl group, or a hydrogen atom, and most preferably a hydrogen atom.

A divalent cyclic group represented $L_1$, $L_2$, and $L_3$ is a divalent linking group having at least one kind of cyclic structure. The ring in the divalent cyclic group is preferably a 5-membered ring, a 6-membered ring, or a 7-membered ring, more preferably a 5-membered ring or a 6-membered ring, and most preferably a 6-membered ring. The ring in the cyclic group may be a fused ring. Note that the ring is more preferably a monocycle rather than the fused ring. In addition, the ring in the cyclic group may be any one of an aromatic ring, an aliphatic ring, or a heterocyclic ring. Examples of the aromatic ring include a benzene ring and a naphthalene ring. Examples of the aliphatic ring include a cyclohexane ring. Examples of the heterocyclic ring include a pyridine ring and a pyrimidine ring. The cyclic group is preferably an aromatic ring or a heterocyclic ring.

Among the divalent cyclic groups represented by $L_1$, $L_2$, and $L_3$, as the cyclic group having a benzene ring, 1,4- phenylene is preferable. As the cyclic group having a naphthalene ring, naphthalene-1,5-diyl or naphthalene-2,6-diyl is preferable. As the cyclic group having a cyclohexane ring, 1,4-cyclohexylene is preferable. As the cyclic group having a pyridine ring, pyridine-2,5-diyl is preferable. As the cyclic group having a pyrimidine ring, pyrimidine-2,5-diyl is preferable.

The divalent cyclic group represented by $L_1$, $L_2$, and $L_3$ may have a substituent. Examples of the substituent include a halogen atom, a cyano group, a nitro group, an alkyl group having 1 to 16 carbon atoms, a halogen-substituted alkyl group having 1 to 16 carbon atoms, an alkoxy group having 1 to 16 carbon atoms, an acyl group having 2 to 16 carbon atoms, an alkylthio group having 1 to 16 carbon atoms, an acyloxy group having 2 to 16 carbon atoms, an alkoxycarbonyl group having 2 to 16 carbon atoms, a carbamoyl group, an alkyl-substituted carbamoyl group having 2 to 16 carbon atoms, and an acylamino group having 2 to 16 carbon atoms.

As $L_1$, $L_2$, and $L_3$, a single bond, *—O—CO—, *—CO—O—, *—CH=CH—, *—C≡C—, *-divalent cyclic group-, *—O—CO-divalent cyclic group-, *—CO—O-divalent cyclic group-, *—CH=CH-divalent cyclic group-, *—C≡C-divalent cyclic group-, *-divalent cyclic group-O—CO—, *-divalent cyclic group-CO—O—, *-divalent cyclic group-CH=CH—, or *-divalent cyclic group-C≡C— is preferable. In particular, a single bond, *—CH=CH—, *—C≡C—, a *—CH=CH-divalent cyclic group-, or a *—C≡C-divalent cyclic group-is preferable. * represents a position bonded to a 6-membered ring including $Y_{11}$, $Y_{12}$, and $Y_{13}$ in Formula (D-2).

$H_1$, $H_2$, and $H_3$ each independently represent a divalent 5-membered cyclic group.

The divalent 5-membered cyclic group is preferably a heterocyclic ring. Examples of the heteroatom include an oxygen atom, a nitrogen atom, a sulfur atom, a boron atom, and a phosphorus atom. In particular, an oxygen atom, a nitrogen atom, or a sulfur atom is preferable, and a heterocyclic ring having a nitrogen atom and an oxygen atom is more preferable.

It is preferable that the divalent 5-membered cyclic group includes at least one methine, and it is more preferable that the divalent 5-membered cyclic group includes two methines. In particular, it is preferable that a hydrogen atom in the methine is substituted with $L^1$, $L^2$, or $L_3$ or $R_1$, $R_2$, or $R_3$.

Examples of the divalent 5-membered cyclic group include thiophene-2,5-diyl, furan-2,5-diyl, oxazole-2,5,-diyl, imidazole-2,5-diyl, 1,3,4-oxadiazole-2,5-diyl, and tetrahydrofuran-2,4-diyl.

The divalent 5-membered cyclic group may have a substituent. Examples of the substituent include the same substituents as those of $Y_{11}$, $Y_{12}$, and $Y_{13}$.

In Formula (D-2), $R_1$, $R_2$, and $R_3$ each independently represent an alkyl group (for example, a methyl group, an ethyl group, an isopropyl group, or a tert-butyl group), an alkenyl group (for example, a vinyl group, an allyl group, a 2-butenyl group, or a 3-pentenyl group), an alkynyl group (for example, a propargyl group or a 3-pentynyl group), an aryl group (for example, a phenyl group, a p-methylphenyl group, or a naphthyl group), a substituted or unsubstituted amino group (for example, an unsubstituted amino group, a methylamino group, a dimethylamino group, a diethylamino group, or an anilino group), an alkoxy group (for example, a methoxy group, an ethoxy group, or a butoxy group), an aryloxy group (for example, a phenyloxy group or a 2-naphthyloxy group), an acyl group (for example, an acetyl group, a benzoyl group, a formyl group, or a pivaloyl group), an alkoxycarbonyl group (for example, a methoxycarbonyl group or an ethoxycarbonyl group), an aryloxycarbonyl group (for example, a phenyloxycarbonyl group), an acyloxy group (for example, an acetoxy group or a benzoyloxy group), an acylamino group (for example, an acetylamino group or a benzoylamino group), an alkoxycarbonylamino group (for example, a methoxycarbonylamino group), an aryloxycarbonylamino group (for example, a phenyloxycarbonylamino group), an alkylsulfonylamino group (for example, a methanesulfonylamino group), an arylsulfonylamino group (for example, a benzenesulfonylamino group), a sulfamoyl group (for example, a sulfamoyl group, an N-methylsulfamoyl group, an N,N-dimethylsulfamoyl group, or an N-phenylsulfamoyl group), a carbamoyl group (for example, an unsubstituted carbamoyl group, an N-methylcarbamoyl group, an N,N-diethylcarbamoyl group, or an N-phenylcarbamoyl group), an alkylthio group (for example, a methylthio group or an ethylthio group), an arylthio group (for example, a phenylthio group), an alkylsulfonyl group (for example, a mesyl group), an arylsulfonyl group (for example, a tosyl group), an alkylsulfinyl group (for example, a methanesulfinyl group), an arylsulfinyl group (for example, a benzenesulfinyl group), a ureido group (for example, an unsubstituted ureido group, a 3-methylureido group, or a 3-phenylureido group), a phosphoric amide group (for example, a diethyl phosphoric amide group or a phenyl phosphoric amide group), a hydroxyl group, a mercapto group, a halogen atom (for example, a fluorine atom, a chlorine atom, a bromine atom, or an iodine atom), a cyano group, a sulfo group, a carboxyl group, a nitro group, a hydroxamic acid group, a sulfino group, a hydrazino group, an imino group, a heterocyclic group (a heterocyclic group having a heteroatom such as a nitrogen atom, an oxygen atom, or a sulfur atom, and examples of the heterocyclic group having a heteroatom include an imidazolyl group, a pyridyl group, a quinolyl group, a furyl group, a piperidyl group, a morpholino group, a benzoxazolyl group, a benzimidazolyl group, and a benzothiazolyl group), or a silyl group (for example, a trimethylsilyl group or a triphenylsilyl group). The substituents may be further substituted with the substituents.

It is more preferable that $R_1$, $R_2$, and $R_3$ are each independently represented by the following Formula (III).

*-$L_{11}$-Q                Formula (III)

In Formula (III), * represents a position bonded to $H_1$, $H_2$, or $H_3$ in Formula (D-2).

Q's each independently a polymerizable group or a methyl group. In a case where the compound represented by Formula (D-2) is used for an optical element where it is preferable that the sizes of retardation and a dichroic ratio do not change depending on heat, for example, for the optical element according to the embodiment of the present invention, it is preferable that Q represents a polymerizable group. The polymerization reaction is preferably addition polymerization (including ring-opening polymerization) or condensation polymerization. In other words, the polymerizable group is preferably a functional group capable of an addition polymerization reaction or a condensation polymerization reaction. Examples of the polymerizable group are shown below.

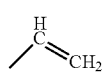

q1

-continued

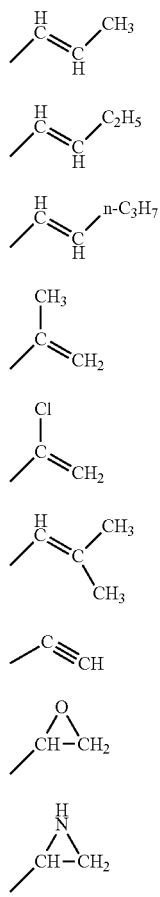

q2
q3
q4
q5
q6
q7
q8
q9
q10

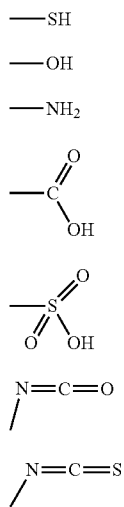

q11
q12
q13
q14
q15
q16
q17

In the above examples, q1 to q10 are preferable, and q1 to q8 are more preferable.

It is more preferable that the polymerizable group is a functional group capable of an addition polymerization reaction. As the polymerizable group, a polymerizable ethylenically unsaturated group or a ring-opening polymerizable group is preferable.

Examples of the polymerizable ethylenically unsaturated group include the following Formulae (M-1) to (M-6).

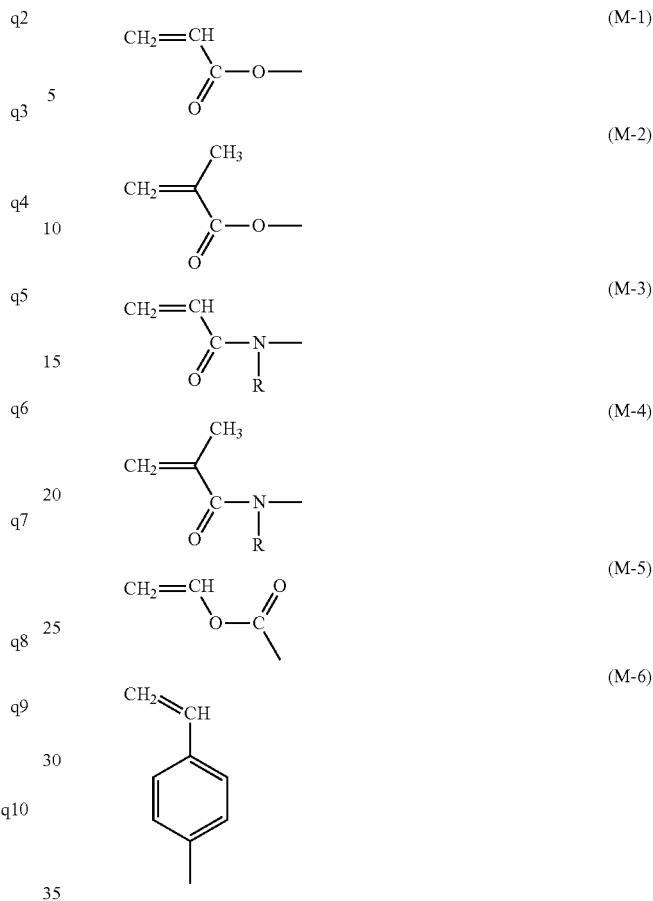

In Formulae (M-3) and (M-4), R represents a hydrogen atom or an alkyl group. It is preferable that R represents a hydrogen atom or a methyl group.

Among Formulae (M-1) to (M-6), (M-1) or (M-2) is preferable, and (M-1) is most preferable.

As the ring-opening polymerizable group, a cyclic ether group is preferable, an epoxy group or an oxetanyl group is more preferable, and an epoxy group is most preferable.

In Formula (III), $L_{11}$ represents a divalent linking group. $L_{11}$ represents preferably a divalent linking group selected from the group consisting of —O—, —S—, —C(=O)—, —NR$_7$—, a divalent chained group, a divalent cyclic group, and a combination thereof. $R_7$ represents an alkyl group having 1 to 7 carbon atoms or a hydrogen atom, preferably an alkyl group having 1 to 4 carbon atoms or a hydrogen atom, and more preferably a methyl group, an ethyl group, or a hydrogen atom, and most preferably a hydrogen atom.

The divalent chained group represented by $L_{11}$ refers to an alkylene group, a substituted alkylene group, an alkenylene group, a substituted alkenylene group, an alkynylene group, or a substituted alkynylene group. In particular, an alkylene group, a substituted alkylene group, an alkenylene group, or an substituted alkenylene group is preferable, and an alkylene group or an alkenylene group is more preferable.

The alkylene group as the divalent chained group represented by $L_{11}$ may be branched. The alkylene group has preferably 1 to 16 carbon atoms, more preferably 2 to 14 carbon atoms, and most preferably 2 to 12 carbon atoms. The alkylene portion of the substituted alkylene group is the same as that of the above-mentioned alkylene group. Examples of the substituent include a halogen atom.

The alkenylene group as the divalent chained group represented by $L_{11}$ may have a substituted or unsubstituted alkylene group at the main chain or may be branched. The alkenylene group has preferably 2 to 16 carbon atoms, more preferably 2 to 14 carbon atoms, and most preferably 2 to 12 carbon atoms. The alkenylene portion of the substituted alkenylene group is the same as that of the alkenylene group. Examples of the substituent include a halogen atom.

The alkynylene group as the divalent chained group represented by $L_{11}$ may have a substituted or unsubstituted alkylene group at the main chain. The alkynylene group has preferably 2 to 16 carbon atoms, more preferably 2 to 14 carbon atoms, and most preferably 2 to 12 carbon atoms. The alkynylene portion of the substituted alkynylene group is the same as that of the alkynylene group. Examples of the substituent include a halogen atom.

Specific examples of the divalent chained group represented by $L_{11}$ include ethylene, trimethylene, tetramethylene, 1-methyl-1,4-butylene, pentamethylene, hexamethylene, octamethylene, nonamethylene, decamethylene, undecamethylene, dodecamethylene, 2-butenylene, and 2-butynylene.

The divalent cyclic group represented $L_{11}$ is a divalent linking group having at least one kind of cyclic structure. The divalent cyclic group is preferably a 5-membered ring, a 6-membered ring, or a 7-membered ring, more preferably a 5-membered ring or a 6-membered ring, and most preferably a 6-membered ring. The ring included in the cyclic group may be a fused ring. Note that the ring is more preferably a monocycle rather than the fused ring. In addition, the ring in the cyclic group may be any one of an aromatic ring, an aliphatic ring, or a heterocyclic ring. Examples of the aromatic ring include a benzene ring and a naphthalene ring. Examples of the aliphatic ring include a cyclohexane ring. Examples of the heterocyclic ring include a pyridine ring and a pyrimidine ring.

Among the divalent cyclic groups represented by $L_{11}$, as the cyclic group having a benzene ring, 1,4-phenylene is preferable. As the cyclic group having a naphthalene ring, naphthalene-1,5-diyl or naphthalene-2,6-diyl is preferable. As the cyclic group having a cyclohexane ring, 1,4-cyclohexylene is preferable. As the cyclic group having a pyridine ring, pyridine-2,5-diyl is preferable. As the cyclic group having a pyrimidine ring, pyrimidine-2,5-diyl is preferable.

The divalent cyclic group represented by $L_{11}$ may have a substituent. Examples of the substituent include a halogen atom, a cyano group, a nitro group, an alkyl group having 1 to 16 carbon atoms, a halogen-substituted alkyl group having 1 to 16 carbon atoms, an alkoxy group having 1 to 16 carbon atoms, an acyl group having 2 to 16 carbon atoms, an alkylthio group having 1 to 16 carbon atoms, an acyloxy group having 2 to 16 carbon atoms, an alkoxycarbonyl group having 2 to 16 carbon atoms, a carbamoyl group, an alkyl-substituted carbamoyl group having 2 to 16 carbon atoms, and an acylamino group having 2 to 16 carbon atoms.

It is still more preferable that $R_1$, $R_2$, and $R_3$ are each independently represented by the following Formula (IV).

$$*\text{-}L_{21}\text{-divalent cyclic group-}L_{22}\text{-}Q_1 \quad \text{Formula (IV)}$$

In Formula (IV), * represents a position bonded to $H_1$, $H_2$, or $H_3$ in Formula (D-2).

$Q^1$ has the same definition as Q in Formula (III).

$L_{21}$ represents a single bond or a divalent linking group. In a case where $L_{21}$ represents a divalent linking group, it is preferable that $L_{21}$ represents a divalent linking group selected from the group consisting of —O—, —S—, —C(=O)—, —CH=CH—, —C≡C—, and a combination thereof. $R_7$ represents an alkyl group having 1 to 7 carbon atoms or a hydrogen atom, preferably an alkyl group having 1 to 4 carbon atoms or a hydrogen atom, and more preferably a methyl group, an ethyl group, or a hydrogen atom, and most preferably a hydrogen atom.

It is preferable that $L_{21}$ represents a single bond, *—O—CO—, *—CO—O—, *—CH=CH—, or *—C≡C— (here, * represents in Formula (IV)).

The divalent cyclic group in Formula (IV) has the same definition as the divalent cyclic group in Formula (III).

$L_{22}$ in Formula (IV) has the same definition as $L_{11}$ in Formula (III).

Examples of the divalent linking group represented by $L_{22}$ are shown below. Here, the right side is bonded to the divalent cyclic group in Formula (IV), and the left side is bonded to $Q_1$.

L-1: -divalent chained group-O-divalent cyclic group-
L-2: -divalent chained group-O-divalent cyclic group-CO—O—
L-3: -divalent chained group-O-divalent cyclic group-O—CO—
L-4: -divalent chained group-O-divalent cyclic group-CO—$NR_7$—
L-5: -divalent chained group-O-divalent cyclic group-divalent chained group-
L-6: -divalent chained group-O-divalent cyclic group-divalent chained group-CO—O—
L-7: -divalent chained group-O-divalent cyclic group-divalent chained group-O—CO—
L-8: -divalent chained group-O—CO-divalent cyclic group-
L-9: -divalent chained group-O—CO-divalent cyclic group-CO—O—
L-10: -divalent chained group-O—CO-divalent cyclic group-O—CO—
L-11: -divalent chained group-O—CO-divalent cyclic group-CO—$NR^7$—
L-12: -divalent chained group-O—CO-divalent cyclic group-divalent chained group-
L-13: -divalent chained group-O—CO-divalent cyclic group-divalent chained group-CO—O—
L-14: -divalent chained group-O—CO-divalent cyclic group-divalent chained group-O—CO—
L-15: -divalent chained group-CO—O-divalent cyclic group-
L-16: -divalent chained group-CO—O-divalent cyclic group-CO—O—
L-17: -divalent chained group-CO—O-divalent cyclic group-O—CO—
L-18: -divalent chained group-CO—O-divalent cyclic group-CO—$NR^7$—
L-19: -divalent chained group-CO—O-divalent cyclic group-divalent chained group-
L-20: -divalent chained group-CO—O-divalent cyclic group-divalent chained group-CO—O—
L-21: -divalent chained group-CO—O-divalent cyclic group-divalent chained group-O—CO—
L-22: -divalent chained group-O—CO—O-divalent cyclic group-
L-23: -divalent chained group-O—CO—O-divalent cyclic group-CO—O—
L-24: -divalent chained group-O—CO—O-divalent cyclic group-O—CO—
L-25: -divalent chained group-O—CO—O-divalent cyclic group-CO—$NR_7$—
L-26: -divalent chained group-O—CO—O-divalent cyclic group-divalent chained group- L-27: -divalent chained group-O—CO—O-divalent cyclic group-divalent chained group-CO—O—

L-28: -divalent chained group-O—CO—O-divalent cyclic group-divalent chained group-O—CO—

L-29: -divalent chained group-

L-30: -divalent chained group-O—

L-31: -divalent chained group-CO—O—

L-32: -divalent chained group-O—CO—

L-33: -divalent chained group-CO—NR$_7$—

L-34: -divalent chained group-O-divalent chained group-

L-35: -divalent chained group-O-divalent chained group-O—

L-36: -divalent chained group-O-divalent chained group-CO—O—

L-37: -divalent chained group-O-divalent chained group-O—CO—

Among these, L-2, L-3, L-9, L-10, L-16, L-17, L-23, L-24, L-30, L-31, L-32, L-35, L-36, or L-37 is preferable.

It is most preferable that R$_1$, R$_2$, and R$_3$ are each independently represented by the following Formula (V).

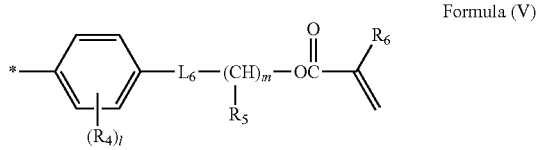

Formula (V)

In Formula (V), * represents a position bonded to H$_1$, H$_2$, or H$_3$ in Formula (D-2).

R$_4$'s each independently represent a halogen atom (preferably a fluorine atom, a chlorine atom, a bromine atom, or an iodine atom), an alkyl group having 1 to 8 carbon atoms, an alkyloxy group having 1 to 8 carbon atoms, an acyl group having 2 to 8 carbon atoms, an acyloxy group having 2 to 8 carbon atoms, an alkoxycarbonyl group having 2 to 8 carbon atoms, a nitro group, or a cyano group. Among these, a halogen atom, an alkyl group having 1 to 3 carbon atoms, an alkyloxy group having 1 to 3 carbon atoms, an acyl group having 2 to 4 carbon atoms, an acyloxy group having 2 to 4 carbon atoms, an alkoxycarbonyl group having 2 to 4 carbon atoms, or a cyano group is preferable.

l represents an integer of 0 to 4, preferably 0 or 1, and most preferably 0. In a case where l represents 2 or more, the groups represented by a plurality of R$_4$'s may be different from each other.

L$_6$ represents —O—, —CO—O—, —O—CO—, —O—CO—O—, or —CH$_2$—, and  represents a position bonded to the benzene ring in Formula (V).

R$_5$ represents a hydrogen atom, a methyl group, an ethyl group, or a propyl group, preferably a hydrogen atom or a methyl group, and most preferably a hydrogen atom.

m represents an integer of 2 to 16 and preferably an integer of 2 to 12.

R$_6$ represents a hydrogen atom or a methyl group and preferably a hydrogen atom.

In addition, it is still more preferable that the disk-like liquid crystal compound is a compound represented by the following Formula (I).

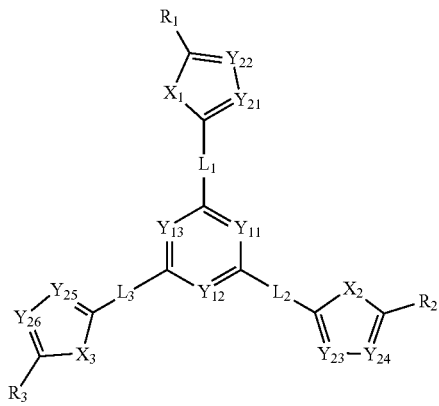

Formula (I)

In Formula (I), Y$_{11}$, Y$_{12}$, Y$_{13}$, Y$_{21}$, Y$_{22}$, Y$_{23}$, Y$_{24}$, Y$_{25}$, and Y$_{26}$ each independently represent methine or a nitrogen atom.

In a case where Y$_{11}$, Y$_{12}$, Y$_{13}$, Y$_{21}$, Y$_{22}$, Y$_{23}$, Y$_{24}$, Y$_{25}$, and Y$_{26}$ represent methine, the methine may have a substituent. Examples of the substituent are the same as the examples of Y$_{11}$, Y$_{12}$, and Y$_{13}$ in Formula (D-2).

In Formula (I), X$_1$, X$_2$, and X$_3$ each independently represent an oxygen atom, a sulfur atom, methylene, or imino. In a case where X$_1$, X$_2$, and X$_3$ represent methylene or imino, the methylene or the imino may have a substituent. As the substituent, the examples of the substituent of the methine described above are preferable. These substituents may be further substituted. In this case, examples of the substituent are the same as those that the substituent of the methine may have.

In Formula (I), the definitions and preferable examples of L$_1$, L$_2$, and L$_3$ are the same as those in Formula (D-2).

In Formula (I), the definitions and preferable examples of R$_1$, R$_2$, and R$_3$ are the same as those in Formula (D-2).

In the present invention, among the compounds represented by Formula (I), a compound represented by Formula (II) where R$_1$, R$_2$, and R$_3$ are each independently represented Formula (V) is preferable.

Examples of a liquid crystal phase that is developed by the compound represented by Formula (I) and a liquid crystalline composition including the compound include those of the liquid crystal phase that satisfy Formula (II). In particular, a columnar phase or a discotic nematic phase is preferable, and a discotic nematic phase is more preferable. The liquid crystal phase is developed preferably in a range of 30° C. to 300° C. and more preferably in a range of 50° C. to 250° C.

Specific examples of the compound represented by Formula (I) or Formula (II) are shown below, but the present invention is not limited thereto.

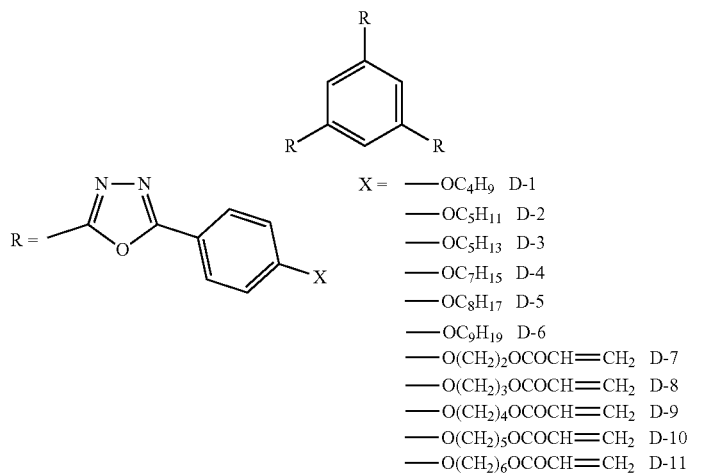

X =
- —OC₄H₉ D-1
- —OC₅H₁₁ D-2
- —OC₅H₁₃ D-3
- —OC₇H₁₅ D-4
- —OC₈H₁₇ D-5
- —OC₉H₁₉ D-6
- —O(CH₂)₂OCOCH=CH₂ D-7
- —O(CH₂)₃OCOCH=CH₂ D-8
- —O(CH₂)₄OCOCH=CH₂ D-9
- —O(CH₂)₅OCOCH=CH₂ D-10
- —O(CH₂)₆OCOCH=CH₂ D-11

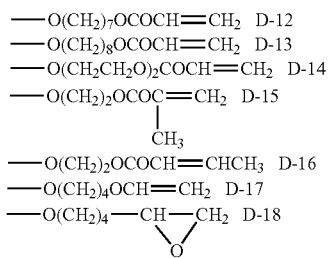

- —O(CH₂)₇OCOCH=CH₂ D-12
- —O(CH₂)₈OCOCH=CH₂ D-13
- —O(CH₂CH₂O)₂COCH=CH₂ D-14
- —O(CH₂)₂OCOC(CH₃)=CH₂ D-15
- —O(CH₂)₂OCOCH=CHCH₃ D-16
- —O(CH₂)₄OCH=CH₂ D-17
- —O(CH₂)₄—CH—CH₂ D-18 (epoxide)

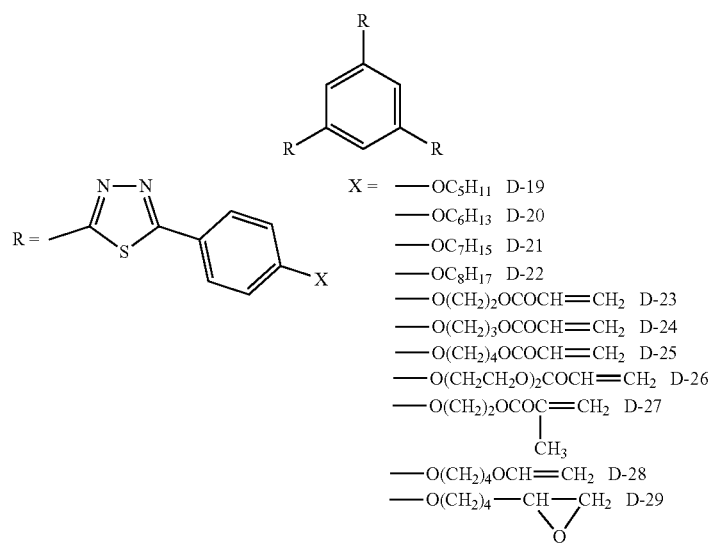

X =
- —OC₅H₁₁ D-19
- —OC₆H₁₃ D-20
- —OC₇H₁₅ D-21
- —OC₈H₁₇ D-22
- —O(CH₂)₂OCOCH=CH₂ D-23
- —O(CH₂)₃OCOCH=CH₂ D-24
- —O(CH₂)₄OCOCH=CH₂ D-25
- —O(CH₂CH₂O)₂COCH=CH₂ D-26
- —O(CH₂)₂OCOC(CH₃)=CH₂ D-27
- —O(CH₂)₄OCH=CH₂ D-28
- —O(CH₂)₄—CH—CH₂ D-29 (epoxide)

-continued

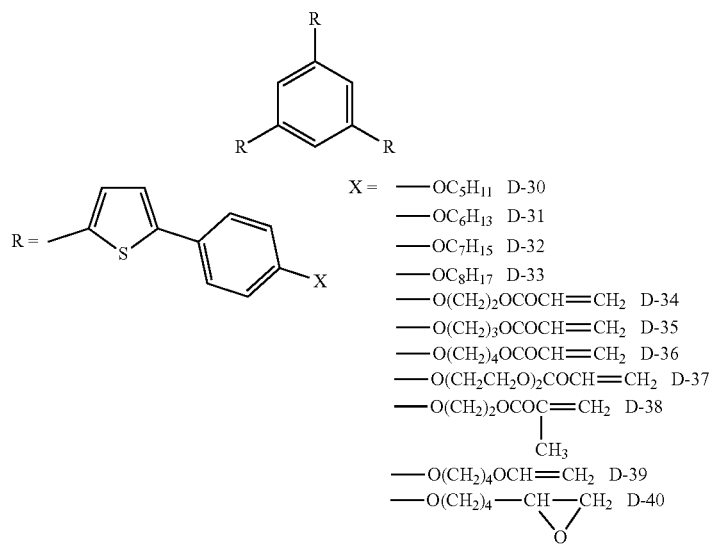

X = —OC₅H₁₁ D-30
—OC₆H₁₃ D-31
—OC₇H₁₅ D-32
—OC₈H₁₇ D-33
—O(CH₂)₂OCOCH=CH₂ D-34
—O(CH₂)₃OCOCH=CH₂ D-35
—O(CH₂)₄OCOCH=CH₂ D-36
—O(CH₂CH₂O)₂COCH=CH₂ D-37
—O(CH₂)₂OCOC(CH₃)=CH₂ D-38
—O(CH₂)₄OCH=CH₂ D-39
—O(CH₂)₄—CH(O)—CH₂ D-40

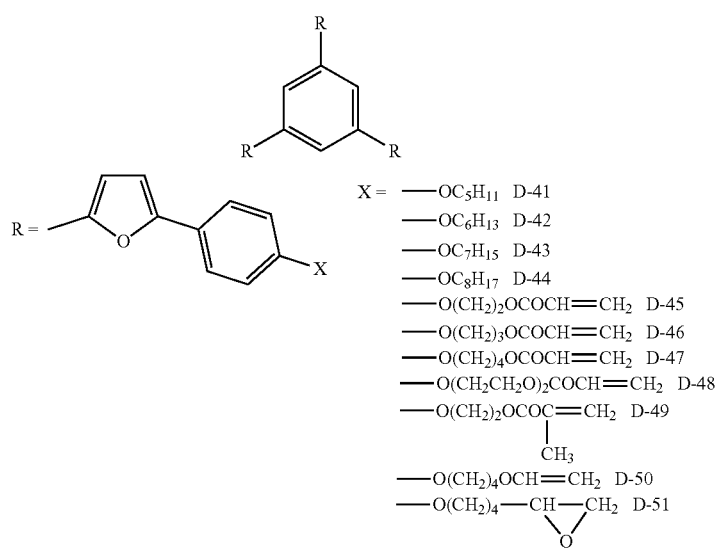

X = —OC₅H₁₁ D-41
—OC₆H₁₃ D-42
—OC₇H₁₅ D-43
—OC₈H₁₇ D-44
—O(CH₂)₂OCOCH=CH₂ D-45
—O(CH₂)₃OCOCH=CH₂ D-46
—O(CH₂)₄OCOCH=CH₂ D-47
—O(CH₂CH₂O)₂COCH=CH₂ D-48
—O(CH₂)₂OCOC(CH₃)=CH₂ D-49
—O(CH₂)₄OCH=CH₂ D-50
—O(CH₂)₄—CH(O)—CH₂ D-51

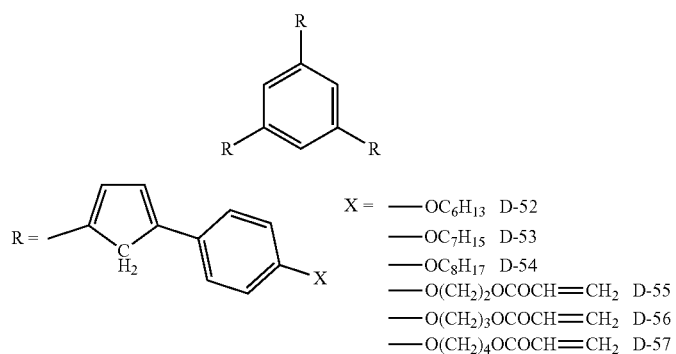

X = —OC₆H₁₃ D-52
—OC₇H₁₅ D-53
—OC₈H₁₇ D-54
—O(CH₂)₂OCOCH=CH₂ D-55
—O(CH₂)₃OCOCH=CH₂ D-56
—O(CH₂)₄OCOCH=CH₂ D-57

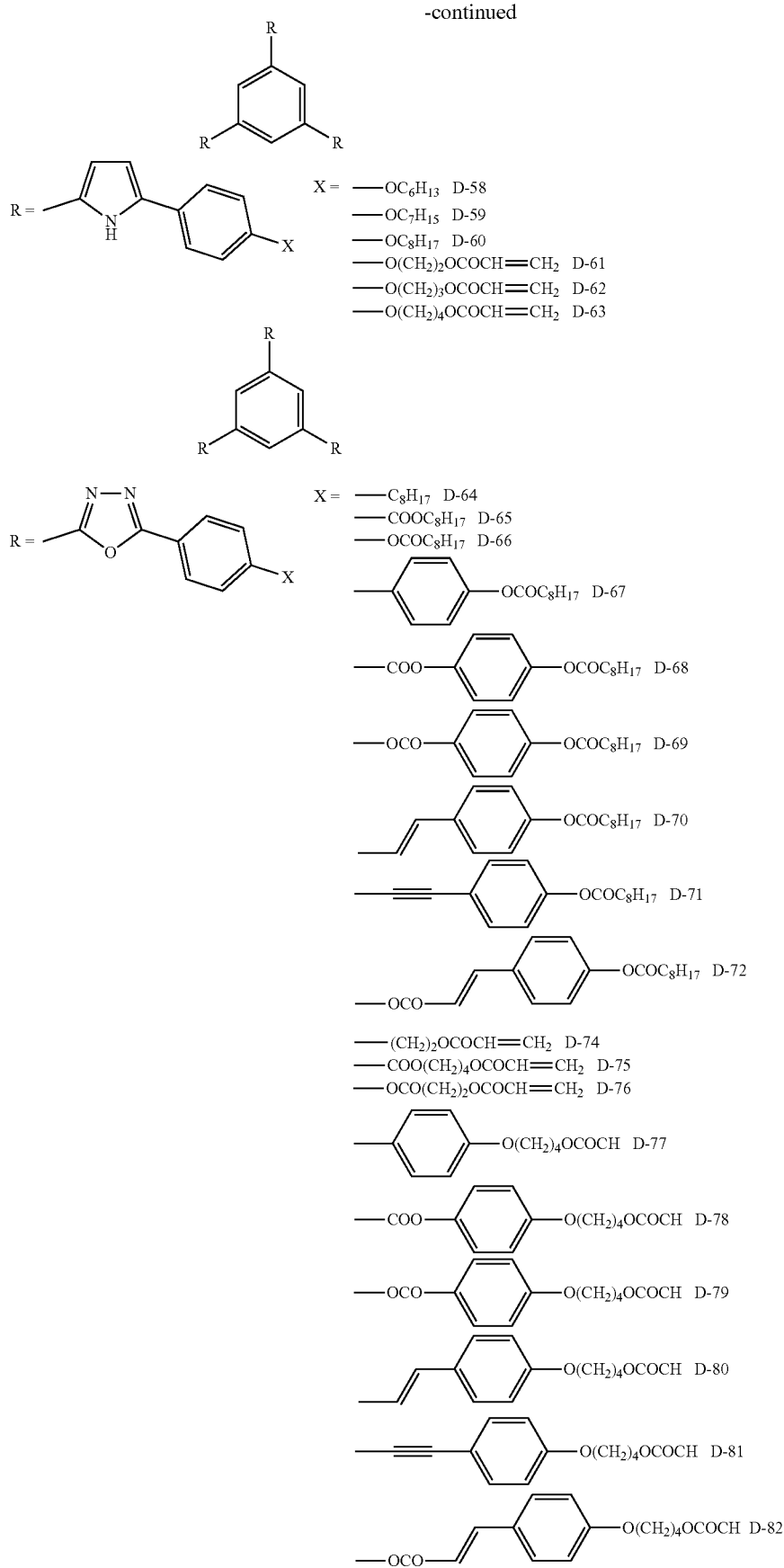

-continued
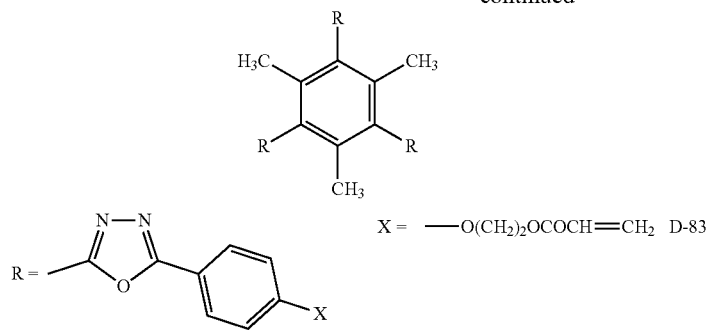
X = —O(CH₂)₂OCOCH=CH₂  D-83
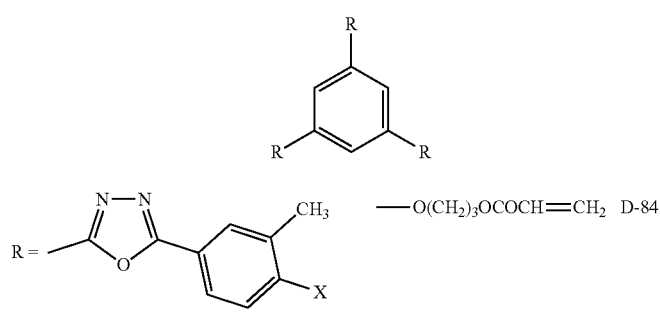
—O(CH₂)₃OCOCH=CH₂  D-84
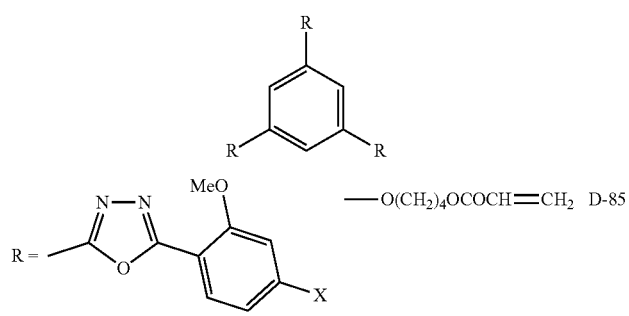
—O(CH₂)₄OCOCH=CH₂  D-85
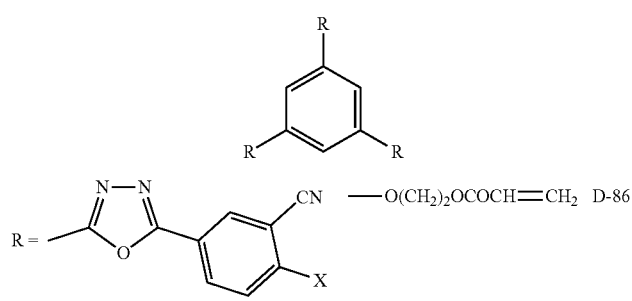
—O(CH₂)₂OCOCH=CH₂  D-86
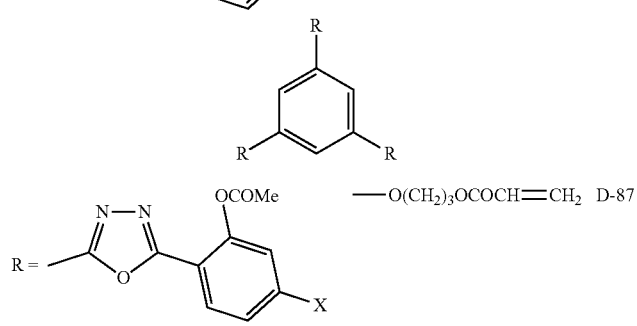
—O(CH₂)₃OCOCH=CH₂  D-87

-continued
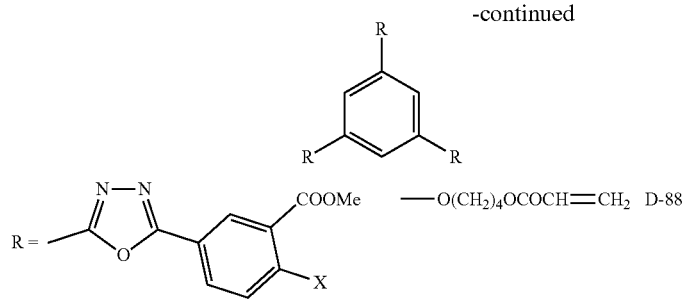
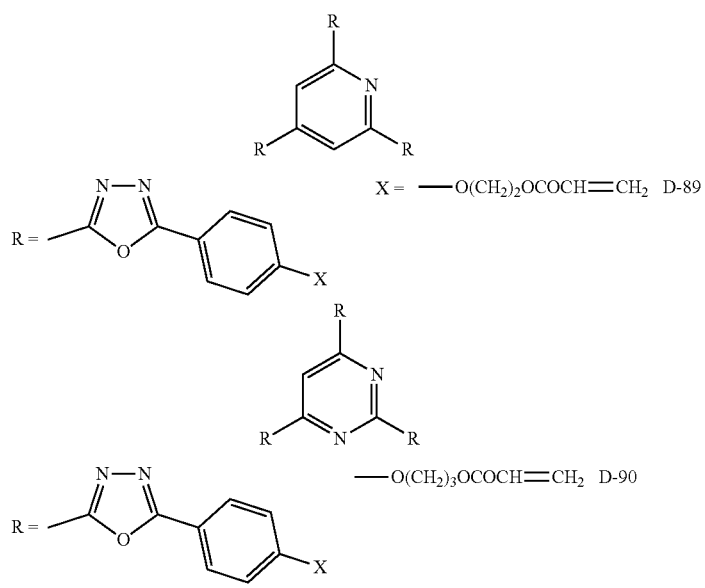
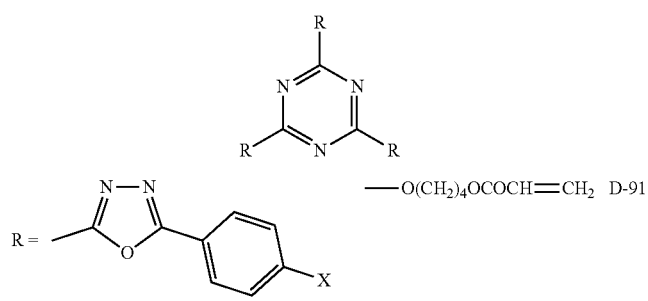
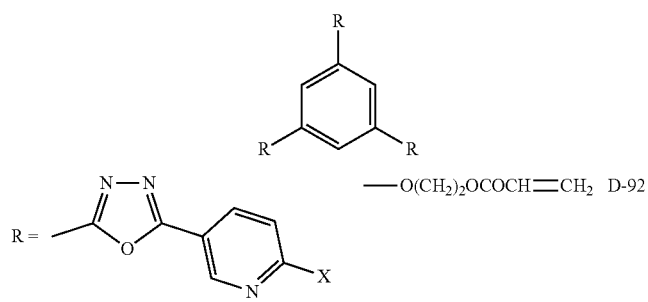

-continued
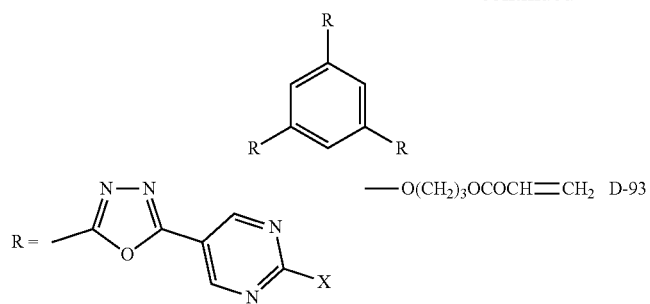
—O(CH₂)₃OCOCH=CH₂ D-93
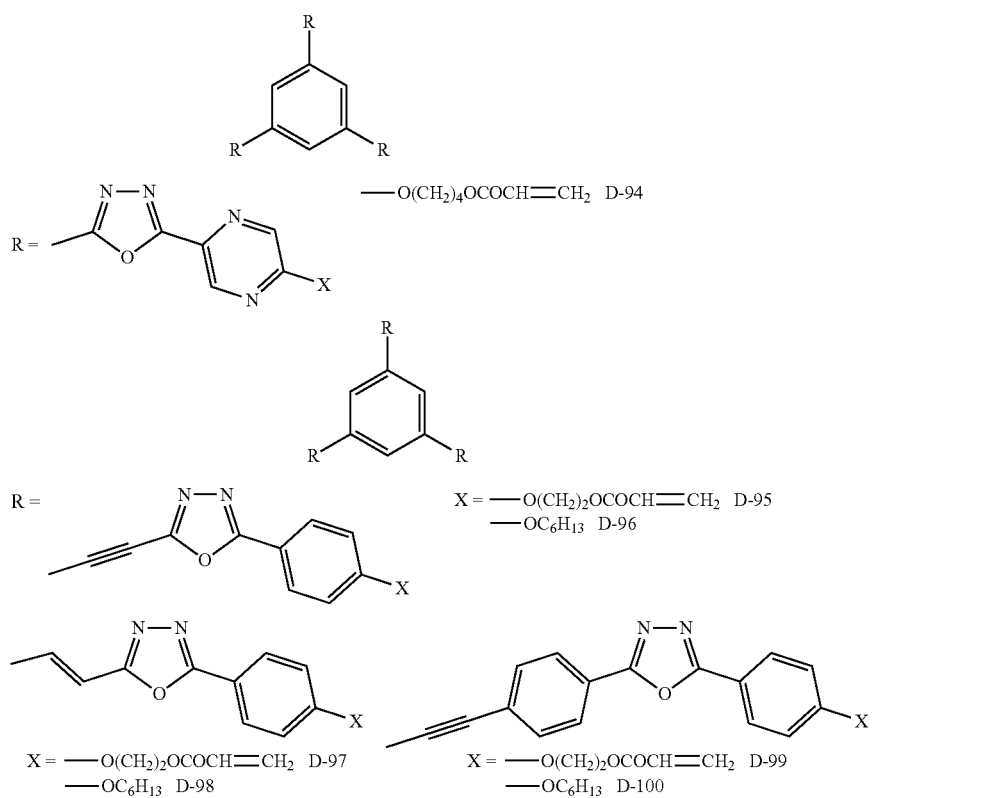
X = —O(CH₂)₂OCOCH=CH₂ D-95
—OC₆H₁₃ D-96
X = —O(CH₂)₂OCOCH=CH₂ D-97
—OC₆H₁₃ D-98
X = —O(CH₂)₂OCOCH=CH₂ D-99
—OC₆H₁₃ D-100
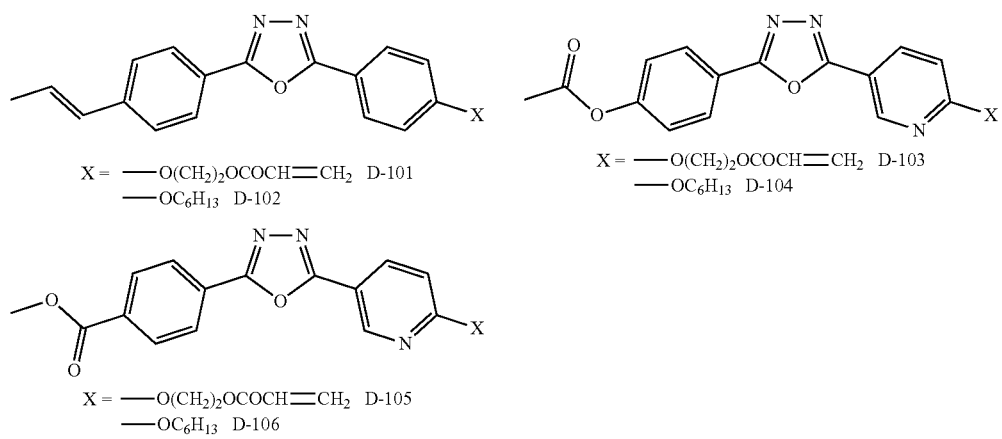
X = —O(CH₂)₂OCOCH=CH₂ D-101
—OC₆H₁₃ D-102
X = —O(CH₂)₂OCOCH=CH₂ D-103
—OC₆H₁₃ D-104
X = —O(CH₂)₂OCOCH=CH₂ D-105
—OC₆H₁₃ D-106
—O(CH₂)₄OCOCH=CH₂ D-94

-continued
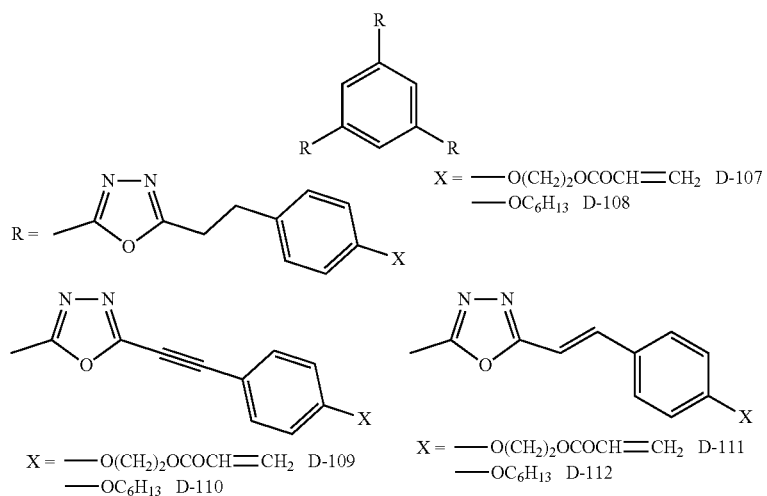
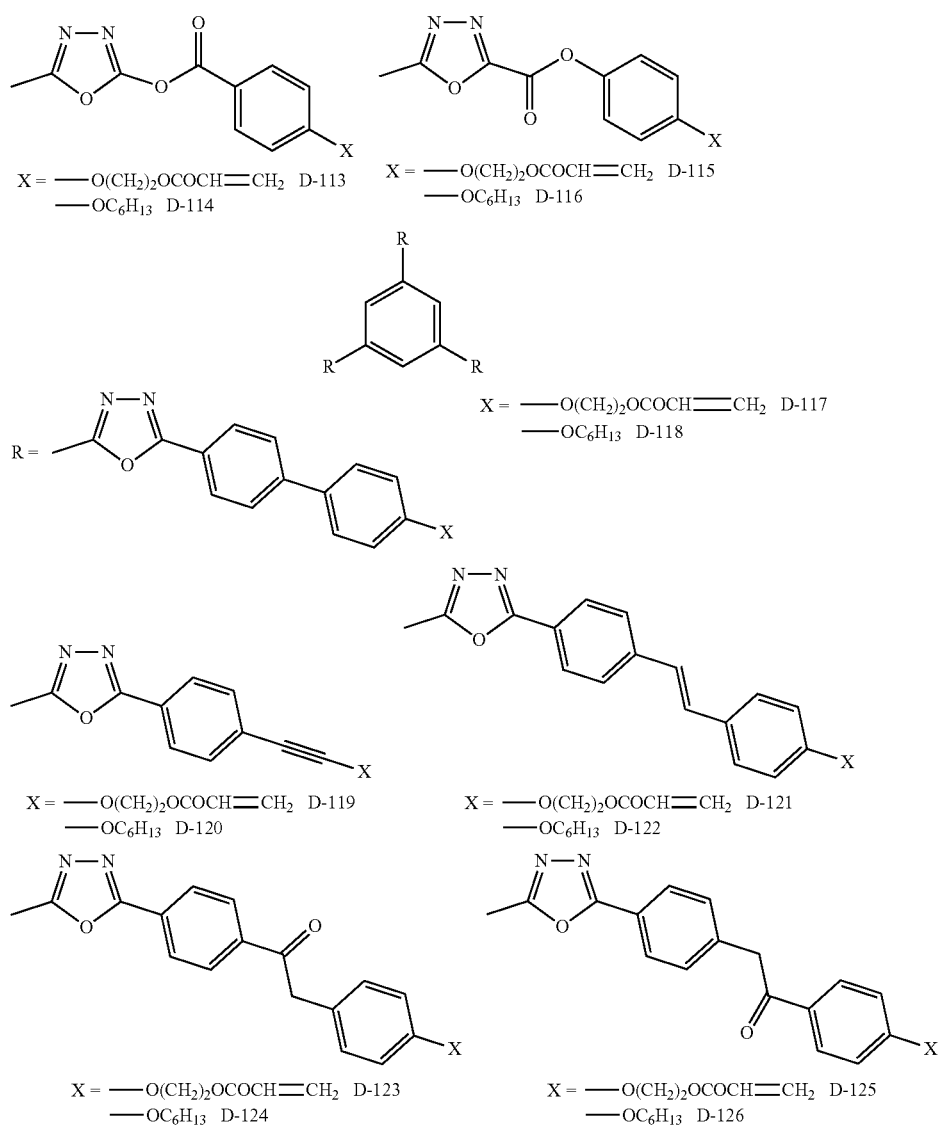

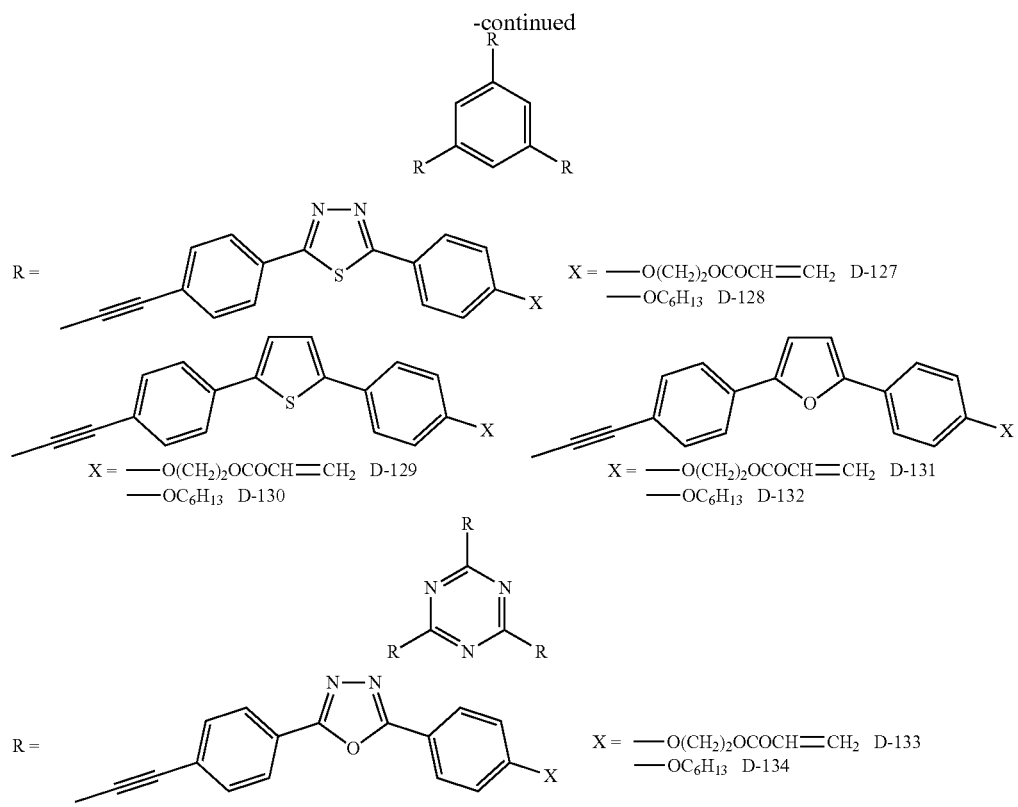

The content of the liquid crystal compound in the composition is not particularly limited and is preferably 50 mass % or more and more preferably 70 mass % or more with respect to the total solid content in the composition. The upper limit is not particularly limited and is 90 mass % or less in many cases.

The total solid content in the composition does not include the solvent.

<Near Infrared Absorbing Dichroic Substance>

The near infrared absorbing dichroic substance is not particularly limited as long as it is a dichroic substance that absorbs near infrared light, and is preferably a dichroic colorant that absorbs near infrared light. The dichroic colorant refers to a colorant having properties in which the absorbance of the molecule in the major axis direction is different from that in the minor axis direction.

Examples of the near infrared absorbing dichroic substance include a diketo pyrrolo pyrrole colorant, a diimmonium colorant, a phthalocyanine colorant, a naphthalocyanine colorant, an azo colorant, a polymethine colorant, an anthraquinone colorant, a pyrylium colorant, a squarylium colorant, a triphenylmethane colorant, a cyanine colorant, and an aminium colorant.

The near infrared absorbing dichroic substances may be used alone or in combination of two or more.

In addition, the dichroic colorant can be classified into a colorant where the molecular shape is a rod-like (hereinafter, abbreviated as "rod-like colorant") and a colorant where the molecular shape is a disk-like (hereinafter, abbreviated as "disk-like colorant"). In the first embodiment of the present invention, the rod-like colorant is preferably used. In the second embodiment of the present invention, the disk-like colorant is preferably used.

Here, the disk-like colorant has a disk-like partial structure in a mother nucleus portion thereof, and the disk-like structure in the mother nucleus excluding side chain portions can be defined by lengths a, b, and c obtained from the following (1) to (4) or the following (1), (2), and (3') to (5').

(1) Regarding the disk-like structure of the disk-like colorant, a molecular structure that is as close to a plane as possible is constructed. As a bond distance and a bond angle, standard values corresponding to orbital hybridization are preferably used. The standard values are described in "Handbook of Chemistry", revised fourth edition, Basic II, Chapter 15 (published by MARUZEN in 1993), edited by The Chemical Society of Japan.

(2) The structure obtained in (1) as an initial value is optimized using a molecular orbital method or a molecular force field method. As the optimization method, Gaussian92, MOPAC93, CHARMm/QUANTA, or MM3 can be applied. In particular, Gausian92 is preferable.

(3) Each of atoms in the optimized disk-like structure is assigned with a sphere defined by van der Waals radius to describe the shape of the molecule.

(4) Three edges of a minimum cuboid where the disk-like structure having the shape obtained in (3) are set to a, b, and c.

In order to reduce arbitrariness, it is preferable to perform the following (3') to (5') instead of (3) and (4).

(3') The centroid of the structure obtained by the structure optimization is moved to an origin, and coordinate axes are set to principal axes of inertia (principal axes of inertia tensor ellipsoid).

(4') Each of the atoms is assigned with a sphere defined by van der Waals radius to describe the shape of the molecule.

(5') Lengths of coordinate axis directions on the van der Waals surface are measured and set to a, b, and c, respectively.

In a case where the disk-like structure is defined by the a, b, and c obtained through the above-described procedure, it is preferable that the disk-like structure satisfies a relationship of a≥b>c and a≥b≥a/2. It is more preferable that the disk-like structure satisfies a relationship of a≥b>c and a≥b≥0.7a. In addition, it is preferable that b/2>c is satisfied.

As the rod-like colorant, an azo colorant, an anthraquinone colorant, a perylene colorant, or a merocyanine colorant is preferable. Examples of the azo colorant include examples described in JP1999-172252A (JP-H11-172252A), examples of the anthraquinone colorant include examples described in JP1996-67822A (JP-H8-67822A), examples of the perylene colorant include examples described in JP1987-129380A (JP-H62-129380A), and examples of the merocyanine colorant examples described in JP2002-241758A. The rod-like colorants may be used alone or in combination of two or more kinds thereof.

In addition, examples of the disk-like colorant include a polarizer using lyotropic liquid crystal represented by OPTIVA Inc., which is known as "E-Type polarizer". For example, materials described in JP2002-90547A can be used. In addition, there is also an example of using a bis azo-based dichroic colorant having a thread-like micelle type structure as a chemical structure that absorbs light in a disk shape, and materials described in JP2002-90526A can be used. These colorants may be used alone or in combination of two or more kinds thereof.

In addition, examples of the disk-like colorant that is suitably used for the second embodiment of the present invention include a compound group having a specific disk-like skeleton as a colorant, for example, a porphyrin nucleus, a phthalocyanine nucleus, a formazan nucleus, or a triphenylmethane nucleus, and a disk-like colorant compound group in which the rod-like dichroic colorant such as an azo colorant is incorporated as a radial side chain into the disk-like skeleton such as a benzene ring or a triphenylene ring described in the discotic liquid crystal molecule. Further, these colorants can be used in combination such that light in a desired wavelength range can be polarized. Regarding the disk-like colorant, various documents are reported (porphyrin nucleus: N. E. Kagen et al., J. Amer. Chem. Soc., vol. 99, page 5484, 1977, phthalocyanine nucleus: "The 28th meeting of The Research Association for Organic Devices, New Development of Sample and Organic Phthalocyanine (Nagao Kobayashi, page 1) and P. A. Stuzhin et al., Inog. Chem., vol. 37, page 2655, 1988, formazan nucleus: Chemistry and application of leuco dyes, Plenium Press, New York, 1997, Ch. 7 Danel S. Daniel, page 207, and triphenylmethane nucleus: Chemistry and application of leuco dyes, Plenium Press, New York, 1997, Ch. 4 I. J. Fletcher, page 97).

In the present invention, it is preferable that the disk-like colorant is a phthalocyanine compound represented by the following Formula (1).

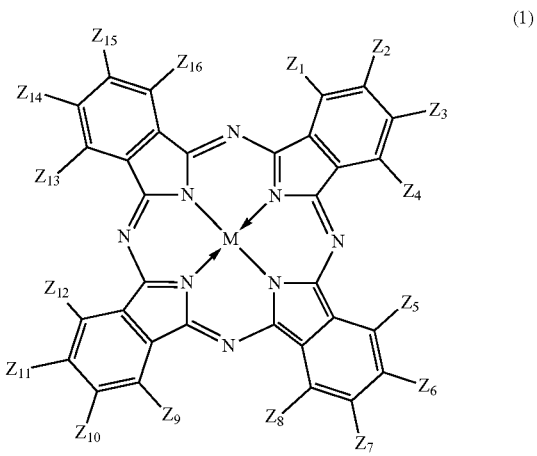

In Formula (1), $Z_1$ to $Z_{16}$ each independently represent a hydrogen atom, a halogen atom, a substituent (a) represented by the following Formula (2), or a substituent (b) represented by the following Formula (3). Note that, among $Z_1$ to $Z_{16}$, 1 to 3.9 Z's represent the substituent (a) or the substituent (b), 3 to 12 Z's represent a hydrogen atom, and the remainder represents a halogen atom. Among 1 to 3.9 Z's representing the substituent (a) or the substituent (b), at least one represents the substituent (a).

In addition, M represents a metal-free compound, a metal, a metal oxide, or a metal halide compound.

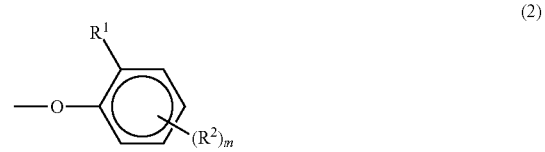

In Formula (2), $R^1$ and $R^2$ may be different from each other and represent a halogen atom or an alkyl group having 1 to 4 carbon atoms, and m represents an integer of 0 to 4.

In addition, in Formula (3), X represents an oxygen atom or a sulfur atom, and Ar represents a phenyl group or a naphthyl group which may be substituted with $R^3$. In this case, $R^3$'s each independently represent a cyano group, a nitro group, OY, a halogen atom, an aryl group, or an alkyl group having 1 to 8 carbon atoms which may be substituted with a halogen atom. In this case, Y represents an alkyl group having 1 to 8 carbon atoms.

Note that, among $Z_1$ to $Z_{16}$ in Formula (1), 1 to 3.9 Z's represent the substituent (a) or the substituent (b), 3 to 12 Z's represent a hydrogen atom, and the remainder represents a halogen atom. Among 1 to 3.9 Z's representing the substituent (a) or the substituent (b), at least one represents the substituent (a).

Here, it is preferable that the remaining halogen atoms are fluorine atoms.

In addition, in the substituent (b), it is preferable that Ar of Formula (3) represents a phenyl group or a naphthyl group where the ortho position is substituted with $R^3$.

In the present invention, it is preferable that the near infrared absorbing dichroic substance has a mesogenic group. In a case where the near infrared absorbing dichroic substance has a mesogenic group, the near infrared absorbing dichroic substance is likely to be aligned along with the above-described liquid crystal compound, and the predetermined absorption properties is likely to be controlled.

The mesogenic group is a functional group having rigidity and aligning properties. Examples of a structure of the mesogenic groups include a structure formed by linking a plurality of groups selected from the group consisting of an aromatic ring group (an aromatic hydrocarbon ring group and an aromatic heterocyclic group) and an alicyclic group directly or through a linking group (for example, —CO—, —O—, and —NR— (R represents a hydrogen atom or an alkyl group), or a group formed by combination of these groups).

In addition, in the present invention, examples of a preferable aspect of the near infrared absorbing dichroic substance include a compound represented by the following Formula (1).

In the compound having the structure represented by Formula (1), an absorption in a visible range is low, and the coloration of the obtained optically-anisotropic layer is further suppressed. In addition, this compound has a group having a mesogenic group, and thus can be easily aligned along with the liquid crystal compound. At this time, the group having a mesogenic group is disposed to extend horizontally from a fused ring portion having a nitrogen atom present at the center of the compound. Therefore, the above-described fused ring portion is likely to be arranged in a direction orthogonal to the slow axis of the formed optically-anisotropic layer. That is, an absorption in an infrared range (in particular, in a wavelength of 700 to 900 nm) derived from the fused ring portion is likely to be obtained in a direction orthogonal to the slow axis of the optically-anisotropic layer, and an optically-anisotropic layer having the desired characteristics is likely to be obtained.

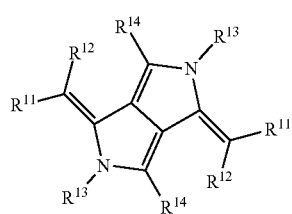

(1)

$R^{11}$ and $R^{12}$ each independently represent a hydrogen atom or a substituent, at least one of $R^{11}$ or $R^{12}$ represents an electron-withdrawing group, and $R^{11}$ and $R^{12}$ may be bonded to each other to form a ring.

Examples of the substituent include an alkyl group, an alkenyl group, an alkynyl group, an aryl group, an amino group, an alkoxy group, an aryloxy group, an aromatic heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, an aromatic heterocyclic thio group, a sulfonyl group, a sulfinyl group, an ureido group, a phosphoric amide group, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group, and a silyl group.

The electron-withdrawing group is a substituent having a positive Hammett's sigma para value (σp value), and examples thereof include a cyano group, an acyl group, an alkyloxycarbonyl group, an aryloxycarbonyl group, a sulfamoyl group, a sulfinyl group, and a heterocyclic group.

These electron-withdrawing groups may further have a substituent.

The Hammett's substituent constant σ value will be described. The Hammett rule is an experimental rule proposed by L. P. Hammett in 1935 in order to quantitatively discuss an effect of a substituent on a reaction or an equilibrium of a benzene derivative. The validity of the Hammett rule is widely admitted nowadays. Substituent constants obtained by the Hammett rule are an σp value and an σm value, and these values can be found in many general books. For example, the detail can be found in "Lange's Handbook of Chemistry" 12th edition, edited by J. A. Dean, 1979 (McGraw-Hill), "Kagaku no Ryoiki (Journal of Japanese Chemistry) special edition" vol. 122, pp. 96-103, 1979 (Nankodo), and "Chem. Rev." vol. 91, pp. 165-195, 1991. In the present invention, a substituent having the Hammett's substituent constant σp value of 0.20 or more is preferable as the electron-withdrawing group. The σp value is preferably 0.25 or more, more preferably 0.30 or more, and still more preferably 0.35 or more. The upper limit is not particularly limited and is preferably 0.80 or less.

Specific examples of the substituent having a Hammett's σp value of 0.2 or higher include a cyano group (0.66), a carboxyl group (—COOH: 0.45), an alkoxycarbonyl group (—COOMe: 0.45), an aryloxycarbonyl group (—COOPh: 0.44), a carbamoyl group (—CONH$_2$: 0.36), an alkylcarbonyl group (—COMe: 0.50), an arylcarbonyl group (—COPh: 0.43), an alkylsulfonyl group (—SO$_2$Me: 0.72), and an arylsulfonyl group (—SO$_2$Ph: 0.68).

In the present specification, Me represents a methyl group, and Ph represents a phenyl group. The values in the parentheses are representative σp values of the substituents extracted from "Chem. Rev." vol. 91, pp. 165-195, 1991.

In a case where $R^{11}$ and $R^{12}$ are bonded to each other to form a ring, it is preferable that the formed ring is a 5- to 7-membered (preferably 5- or 6-membered) ring which is typically used as an acid nucleus in a merocyanine colorant.

It is preferable that the ring which is formed by $R^{11}$ and $R^{12}$ being bonded to each other is a 1,3-dicarbonyl nucleus, a pyrazolinone nucleus, a 2,4,6-triketohexahydropyrimidine nucleus (including a thioketone form), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, a 3,5-pyrazolidinedione nucleus, a benzothiophen-3-one nucleus, or an indanone nucleus.

It is preferable that $R^{11}$ represent a heterocyclic group. As the heterocyclic group, a pyrazole ring group, a thiazole ring group, an oxazole ring group, an imidazole ring group, an oxadiazole ring group, a thiadiazole ring group, a triazole ring group, a pyridine ring group, a pyridazine ring group, a pyrimidine ring group, a pyrazine ring group, a benzo fused ring group thereof, a naphtho fused ring group, or a fused ring complex thereof is preferable.

$R^{13}$'s each independently represent a hydrogen atom, an alkyl group, an aryl group, a heteroaryl group, substituted boron, or a metal atom and may form a covalent bond or a coordinate bond with $R^{11}$.

The substituent of the substituted boron represented by $R^{13}$ has the same definition as that described above regarding $R^{11}$ and $R^{12}$, and is preferably an alkyl group, an aryl group, or a heteroaryl group.

In addition, as the metal atom represented by $R^{13}$, a transition metal atom, a magnesium atom, an aluminum atom, a calcium atom, a barium atom, a zinc atom, or a tin atom is preferable, and an aluminum atom, a zinc atom, a tin atom, a vanadium atom, an iron atom, a cobalt atom, a nickel atom, a copper atom, a palladium atom, an iridium atom, or a platinum atom is more preferable.

$R^{14}$'s each independently represent a group having a mesogenic group. The definition of the mesogenic group is as described above.

It is preferable that $R^{14}$ represents a group represented by the following Formula (2). * represents a bonding position.

$*-M^1-(X^1-M^2)_n-X^2-P$      Formula (2)

$M^1$ represents a substituted or unsubstituted arylene group or a substituted or unsubstituted heteroarylene group. Examples of the arylene group include a phenylene group.

$X^1$ and $X^2$ each independently represent a single bond, —O—, —CO—, —CH$_2$—, —CH=CH—, —C≡C—, —NR$^o$—, or a combination thereof (for example, —O—CO— or —CH$_2$—CH$_2$—). $R^o$ represents a hydrogen atom or an alkyl group having 1 to 5 carbon atoms.

$M^2$ represents a substituted or unsubstituted arylene group, a substituted or unsubstituted heteroarylene group, or a substituted or unsubstituted cycloalkylene group.

n represents 1 to 5. In particular, it is preferable that n represents 2 to 4.

P represents a hydrogen atom or a polymerizable group. The definition of the polymerizable group is the same as that of the polymerizable group which may be included in the above-described liquid crystal compound.

It is more preferable that the near infrared absorbing dichroic substance is a compound represented by the following Formula (3).

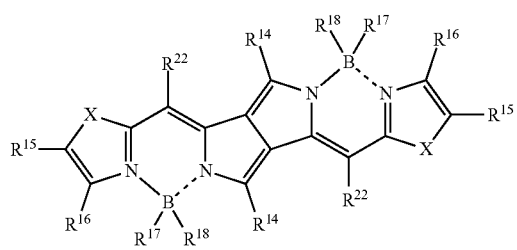

(3)

The definition of $R^{14}$ is as described above.

$R^{22}$'s each independently represent a cyano group, an acyl group, an alkoxycarbonyl group, an alkylsulfinyl group, an arylsulfinyl group, or a nitrogen-containing heteroaryl group.

$R^{15}$ and $R^{16}$ each independently represent a hydrogen atom, an alkyl group, an alkoxy group, an aryl group, or a heteroaryl group, and $R^{15}$ and $R^{16}$ may be bonded to each other to form a ring. Examples of the formed ring include an alicyclic ring having 5 to 10 carbon atoms, an aryl ring having 6 to 10 carbon atoms, and a heteroaryl ring having 3 to 10 carbon atoms.

$R^{17}$ and $R^{18}$ each independently represent an alkyl group, an alkoxy group, an aryl group, or a heteroaryl group.

X's each independently represent an oxygen atom, a sulfur atom, —NR—, —CRR'—, or —CH=CH—, and R and R' each independently represent a hydrogen atom, an alkyl group, or an aryl group.

The content of the near infrared absorbing dichroic substance in the composition is not particularly limited, and is preferably 5% to 70 mass % and more preferably 10% to 50 mass % with respect to the total mass of the liquid crystal compound from the viewpoint of further improving the effects of the present invention.

<Other Components>

The above-described composition may include components other than the liquid crystal compound and the near infrared absorbing dichroic substance.

The composition may include a polymerization initiator. The polymerization initiator to be used is selected depending on the type of the polymerization reaction, and examples thereof include a thermal polymerization initiator and a photopolymerization initiator. Examples of the photopolymerization initiator as the polymerization initiator include an α-carbonyl compound, acyloin ether, an a-hydrocarbon-substituted aromatic acyloin compound, a polynuclear quinone compound, and a combination of a triarylimidazole dimer and p-aminophenyl ketone.

The content of the polymerization initiator in the composition is preferably 0.01% to 20 mass % and more preferably 0.5% to 10 mass % with respect to the total solid content of the composition.

In addition, the composition may include a polymerizable monomer.

Examples of the polymerizable monomer include a radically polymerizable compound or a cationically polymerizable compound. In particular, a polyfunctional radically polymerizable monomer is preferable. In addition, as the polymerizable monomer, a monomer which is copolymerizable with the liquid crystal compound having a polymerizable group is preferable. Examples of the polymerizable monomer include compounds described in paragraphs "0018" to "0020" in JP2002-296423A.

The content of the polymerizable monomer in the composition is preferably 1% to 50 mass % and more preferably 2% to 30 mass % with respect to the total mass of the liquid crystal compound.

In addition, the composition may include a surfactant. Examples of the surfactant include a well-known compound of the related art. In particular, a fluorine compound is preferable. Examples of the surfactant include a compound described in paragraphs "0028" to "0056" of JP2001-330725A and a compound described in paragraphs "0069" to "0126" of JP2003-295212A.

In addition, the composition may include a solvent. As the solvent, an organic solvent is preferable. Examples of the organic solvent include amides (for example, N,N-dimethylformamide), sulfoxides (for example, dimethyl sulfoxide), heterocyclic compounds (for example, pyridine), hydrocarbons (for example, benzene or hexane), alkyl halides (for example, chloroform or dichloromethane), esters (for example, methyl acetate, ethyl acetate, or butyl acetate), ketones (for example, acetone or methyl ethyl ketone), and ethers (for example, tetrahydrofuran or 1,2-dimethoxyethane). Two or more organic solvents may be used in combination.

In addition, the composition may include various alignment control agents such as an air interface alignment agent, a vertical alignment agent, or a horizontal alignment agent. These alignment control agents are compounds that can control horizontal or vertical alignment of the liquid crystal compound on an interface side.

Here, as the air interface alignment agent, for example, fluoropolymers (X) and (Y) described in paragraphs "0016" to "0057" of JP2015-206010A or a copolymer obtained by copolymerizing monomers forming the fluoropolymers (X) and (Y) are suitably used.

Further, the composition may include an adherence improving agent, a plasticizer or a polymer other than the above-described components.

<Forming Method>

A method of forming the optical element using the above-described composition is not particularly limited and examples thereof include a well-known method.

In particular, from the viewpoint of easily controlling in-plane retardation, a method including applying a composition including a liquid crystal compound having a polymerizable group (hereinafter, simply also referred to as "polymerizable liquid crystal compound") and a near infrared absorbing dichroic substance to form a coating film, aligning the coating film to align the polymerizable liquid crystal compound, and curing (an ultraviolet radiation treatment (light irradiation treatment) or a heat treatment) the obtained coating film to form an optically-anisotropic layer is preferable.

Hereinafter, the procedure of the method will be described in detail.

First, the composition is applied to a support to form a coating film, and the coating film is aligned to align the polymerizable liquid crystal compound.

The composition to be used includes a polymerizable liquid crystal compound. The definition of the polymerizable liquid crystal compound is as described above.

The support to be used is a member having a function as a substrate to which the composition is applied. The support may be a temporary support that is peeled off after applying and curing the composition.

As the support (temporary support), for example, a plastic film or a glass substrate may be used. Examples of a material forming the plastic film include a polyester resin such as polyethylene terephthalate (PET), a polycarbonate resin, a (meth)acrylic resin, an epoxy resin, a polyurethane resin, a polyamide resin, a polyolefin resin, a cellulose derivative, a silicone resin, and polyvinyl alcohol (PVA).

The thickness of the support only needs to be about 5 to 1000 µm and is preferably 10 to 250 µm and more preferably 15 to 90 µm.

Optionally, an alignment layer may be disposed on the support.

The alignment layer generally includes a polymer as a major component. The polymer for the alignment layer is described in many documents, and a plurality of commercially available products are available. As the polymer for the alignment layer, polyvinyl alcohol, polyimide, or a derivative thereof is preferable.

It is preferable that a well-known rubbing treatment is performed on the alignment layer.

In the present invention, from the viewpoint of prevent deterioration in surface condition caused by non-contact with the alignment film surface during the formation of the alignment layer, a photo-alignment film is also preferably used as the alignment layer.

The photo-alignment film is not particularly limited, but a polymer material such as a polyamide compound or a polyimide compound described in paragraphs "0024" to "0043" of WO2005/096041A; a liquid crystal alignment film that is formed of a liquid crystal aligning agent having a photo-aligned group described in JP2012-155308A; a photo-alignment film described in WO2019/225632A; a photo-alignment film described in WO2020/179864A; LPP-JP265CP (trade name, manufactured by Rolic Technologies Ltd.), or the like can be used.

In addition, in the present invention, the thickness of the alignment layer is not particularly limited and, from the viewpoint of forming an optical element having a uniform film thickness by alleviating the surface unevenness that may be present on the support, is preferably 0.01 to 10 µm, more preferably 0.01 to 1 µm, and still more preferably 0.01 to 0.5 µm.

Examples of a method of applying the composition include a curtain coating method, a dip coating method, a spin coating method, a printing coating method, a spray coating method, a slot coating method, a roll coating method, a slide coating method, a blade coating method, a gravure coating method, and a wire bar method. Even in a case where the composition is applied using any of the methods, single layer coating is preferable.

The coating film formed on the support is aligned to align the polymerizable liquid crystal compound in the coating film.

The alignment treatment can be performed by drying the coating film at room temperature or by heating the coating film. In the case of a thermotropic liquid crystal compound, the liquid crystal phase formed by the alignment treatment can generally be transferred by a change in temperature or pressure. In the case of a lyotropic liquid crystal compound, a liquid crystal phase formed by the alignment treatment can also be transferred by a compositional ratio such as the amount of a solvent.

In a case where the coating film is heated, conditions are not particularly limited, and the heating temperature is preferably 50° C. to 250° C. and more preferably 50° C. to 150° C., and the heating time is preferably 10 seconds to 10 minutes.

In addition, before performing a curing treatment (light irradiation treatment) after heating the coating film, optionally, the coating film may be cooled. The cooling temperature is preferably 20° C. to 200° C. and more preferably 30° C. to 150° C.

A difference between the heating temperature of the coating film and the cooling temperature of the coating film is not particularly limited and is preferably 40° C. or higher. The upper limit is not particularly limited and is, for example, 150° C. or lower.

In a case where the coating film is heated and cooled before performing the curing treatment, it is preferable that the heating temperature $T_A$ of the coating film is 50° C. to 250° C. and the cooling temperature $T_B$ is in a range of the heating temperature $T_A \times 0.4$ to the heating temperature $T_A \times 0.7$.

Next, the coating film in which the polymerizable liquid crystal compound is aligned is cured.

A method of curing the coating film in which the polymerizable liquid crystal compound is aligned is not particularly limited, and examples thereof include a light irradiation treatment and a heat treatment. Among these, from the viewpoint of manufacturing suitability, a light irradiation treatment is preferable, and an ultraviolet irradiation treatment is more preferable.

radiation conditions of the light irradiation treatment are not particularly limited, and an irradiation dose of 50 to 1000 mJ/cm² is preferable.

In the forming method, the arrangement state of the near infrared absorbing dichroic substance, and the like can be adjusted by adjusting various conditions. As a result, the optical characteristics of the optically-anisotropic layer can be adjusted.

For example, by adjusting the heating temperature in a case where the liquid crystal compound is aligned after applying the composition to the support to form the coating film and adjusting the cooling temperature in a case where the coating film is heated and cooled, the arrangement state of the near infrared absorbing dichroic substance, and the like can be adjusted. As a result, the optical characteristics of the optically-anisotropic layer can be adjusted.

[Light Source]

It is preferable that the fingerprint recognition sensor according to the embodiment of the present invention includes a light emitting element as a light source.

Examples of the light emitting element include a light emitting diode (LED) and a laser diode (LD).

In addition, it is preferable that the light emitting element emits ultraviolet light or light in a blue light range. Specifically, it is preferable that the light emitting element has a peak of an emission spectrum in a wavelength range of 200 nm to 500 nm, and it is more preferable that the light emitting element has a peak of an emission spectrum in a wavelength range of 380 nm to 500 nm.

In addition, it is also preferable that the light emitting element is an infrared light emitting element that emits light in an infrared range. Specifically, it is preferable that the light emitting element is an infrared light emitting element that has a peak of an emission spectrum in a wavelength range of 780 nm to 1400 nm, and it is more preferable that the light emitting element is an infrared light emitting element that has a peak of an emission spectrum in a wavelength range of 780 nm to 1100 nm.

[Optical Element]

An optical element according to a first aspect of the present invention is an optical element comprising: first layer that includes a near infrared absorbing dichroic substance and has an absorption axis with respect to near infrared light in an in-plane direction; and a second layer that includes a near infrared absorbing dichroic substance and has an absorption axis with respect to near infrared light in a thickness direction.

The optical element according to the first aspect of the present invention is the same as described in the second embodiment of the fingerprint recognition sensor according to the present invention.

An optical element according to a second aspect of the present invention is an optical element comprising: an optically-anisotropic layer that is formed of a composition including a near infrared absorbing dichroic substance, a liquid crystal compound, and an alignment control agent, in which the near infrared absorbing dichroic substance is a disk-like colorant, the liquid crystal compound is a disk-like liquid crystal compound, and the alignment control agent is an air interface alignment agent.

In addition, in the optical element according to the second aspect of the present invention, the disk-like colorant is disposed in a state where the disk-like colorant is aligned to be perpendicular and uniaxial to a surface of the optically-anisotropic layer (hereinafter, also abbreviated as perpendicular uniaxial alignment), and the disk-like liquid crystal compound is immobilized in a state where the disk-like liquid crystal compound is aligned to be perpendicular and uniaxial to the surface of the optically-anisotropic layer.

The disk-like colorant, the disk-like liquid crystal compound, and the air interface alignment agent in the composition and the method of forming the optically-anisotropic layer using the composition are the same as described in the fingerprint recognition sensor according to the embodiment of the present invention.

In the present invention, the perpendicular uniaxial alignment of the disk-like colorant refers to a positional relationship where a disk-like plane of the disk-like colorant is substantially perpendicular to a disk-like plane of the disk-like liquid crystal compound and is substantially parallel to the disk-like plane of the disk-like liquid crystal compound (a positional relationship where the former plane is in a range of 0 to 30 degrees with respect to latter plane).

In addition, the perpendicular uniaxial alignment of the disk-like liquid crystal compound refers to a state where an optical axis of the disk-like liquid crystal compound is aligned to be perpendicular to a substrate surface in a substantially uniform direction (is aligned in an angle range of 50 to 90 degrees).

Here, perpendicular uniaxial alignment of the disk-like colorant can be checked by absorption anisotropy at $\lambda$max of the colorant in an infrared range.

Specifically, the absorption anisotropy of the optical element can be acquired by measuring the polar angle dependence of absorption properties.

More specifically, by using an ultraviolet-visible-near infrared spectrophotometer V-660 including an automatic absolute reflectivity measuring unit ARMN-735 (manufactured by Jasco Corporation) as a measuring device, at an azimuthal angle orthogonal to an absorption axis present in a plane (xy plane), an absorption spectrum is measured while the normal direction polar angle in a range of −50° to 0° at an interval of 10°, the degree of absorption anisotropy, that is, kz−kx is obtained by fitting. A state where kz−kx=0 can be evaluated as the state where the disk-like colorant is in the perpendicular uniaxial alignment. Note that kx represents an absorbance in the in-plane absorption axis, and kz represents an absorbance in an out-of-plane direction.

In addition, the perpendicular uniaxial alignment of the disk-like liquid crystal compound can be checked by any one of the absorption anisotropy at $\lambda$max of the disk-like liquid crystal compound, the observation of the cross-section with a polarization microscope, or the configuration where the optical characteristics of the optically-anisotropic layer is a negative A-Plate. Each of the check methods will be described below.

<Absorption Anisotropy>

The absorption anisotropy of the optical element can be acquired by measuring the polar angle dependence of polarization characteristics.

Specifically, by using Axoscan (manufactured by Axometrics, Inc.) as a measuring device, at an azimuthal angle (azimuthal angle indicated by a broken line in FIG. 9) orthogonal to the absorption axis (or the in-plane slow axis) of the disk-like liquid crystal compound, a Mueller matrix is measured while the normal direction polar angle in a range of −50° to 0° at an interval of 10°, and the degree of absorption anisotropy, that is, kz−kx is obtained by fitting. A state where kz−kx=0 can be evaluated as the state where the disk-like liquid crystal compound is in the perpendicular uniaxial alignment. Note that kx represents an absorbance in the in-plane absorption axis, and kz represents an absorbance in an out-of-plane direction.

<Observation with Polarization Microscope>

A cross-section taken along the slow axis in the in-plane direction is observed by transmission microscopy using a polarization microscope, and a state not having retardation can be evaluated as a state where the disk-like liquid crystal is in the perpendicular uniaxial alignment.

<Optical Characteristics of Optically-Anisotropic Layer>

Using AxoScan OPMF-1 (manufactured by Opto Science Inc.), a three-dimensional refractive index of the film at a wavelength of 550 nm is measured, and an average refractive index $((nx+ny+nz)/3)$ and a film thickness (d (μm)) are input to AxoScan such that the values of nx, ny, and nz can be calculated. In the negative A-Plate, the value of the Nz factor expressed in the following expression is assumed as 0.

$$Nz=(nx-nz)/(nx-ny)$$

nx during the calculation of the Nz factor of the optically-anisotropic layer represents a refractive index in an in-plane slow axis direction of the optically-anisotropic layer, ny during the calculation of the Nz factor of the optically-anisotropic layer represents a refractive index in an in-plane fast axis direction of the optically-anisotropic layer, and nz during the calculation of the Nz factor of the optically-anisotropic layer represents a refractive index in a thickness direction of the optically-anisotropic layer.

In the optical element according to the second aspect of the present invention, from the viewpoint of easily improving the sensitivity and the S/N ratio, it is preferable that the disk-like colorant has a maximal absorption wavelength in a wavelength range of 800 to 1000 nm.

In the present specification, the maximal absorption wavelength refers to a maximal absorption wavelength in the absorption spectrum measured using the following method.

<Measuring Method>

5 parts by mass of the disk-like colorant as a measurement target and 100 parts by mass of the disk-like liquid crystal compound are dissolved in 660 parts by mass of chloroform to prepare a solution having a concentration of solid contents of 14 mass %.

Next, the prepared solution is applied to a glass substrate by spin coating (1000 rpm, 10 seconds) to prepare a liquid crystal film including the disk-like colorant. By using an ultraviolet-visible-near infrared spectrophotometer V-660 (manufactured by Jasco Corporation; JASCO), the absorbance of the prepared liquid crystal film in a wavelength range of 200 to 1500 nm is measured.

Next, the maximal absorption wavelength is acquired in the obtained absorption spectrum.

In the optical element according to the second aspect of the present invention, from the viewpoint of easily improving the sensitivity, it is preferable that a dichroic ratio in an in-plane direction is 5 or more.

Here, by using an ultraviolet-visible-near infrared spectrophotometer V-660 including an automatic absolute reflectivity measuring unit ARMN-735 (manufactured by Jasco Corporation), the absorbance of the anisotropic organic film is measured to calculate the dichroic ratio from the following expression.

$$\text{Dichroic Ratio}=Az0/Ay0$$

Az0: an absorbance of a light absorption anisotropic film with respect to polarized light in an in-plane absorption axis direction Ay0: an absorbance of a light absorption anisotropic film with respect to polarized light in an in-plane transmission axis direction In a case where the optical element according to the second aspect of the present invention is bonded to a display, from the viewpoint of preventing visibility from being obstructed, it is preferable that a color is neutral gray.

Here, the state where the color is neutral gray refers to a state where coordinate values L, a, and b satisfy $22 \leq L \leq 70$, $-2.0 \leq a \leq 2.0$, and $-2.0 \leq b \leq 2.0$, respectively, and an average value of spectroscopic transmittance in a wavelength of 400 to 700 nm is within ±30%.

EXAMPLES

The present invention will be described in more detail using Examples. Materials, used amounts, ratios, treatment details, treatment procedures, and the like shown in the following Examples can be appropriately changed within a range not departing from the scope of the present invention. Accordingly, the scope of the present invention is not limited to the following examples.

Example 1

[Preparation of Optical Element]

A cellulose acylate film T1 ("TD40UL", manufactured by FUJIFILM Corporation) was caused to pass through a gap between dielectric heating rolls at a temperature of 60° C. to increase a film surface temperature to 40° C.

Next, an alkali solution having a composition shown below was applied to a single surface of the film using a bar coater in an application amount of 14 ml/m$^2$, and the film was heated to 110° C.

Next, the obtained film was transported for 10 seconds under a steam far infrared heater (manufactured by Noritake Co., Ltd.).

Next, pure water was applied to the surface of the obtained film at 3 ml/m$^2$ using the same bar coater.

Next, water cleaning using a foundry coater and water draining using an air knife were repeated on the obtained film three times, and subsequently the film was transported to and dried in a drying zone at 70° C. for 10 seconds. As a result, the cellulose acylate film on which the alkali saponification treatment was performed was prepared as a support.

| (Alkali Solution) | |
|---|---|
| Potassium hydroxide | 4.7 parts by mass |
| Water | 15.8 parts by mass |
| Isopropanol | 63.7 parts by mass |
| Surfactant ($C_{14}H_{29}O(CH_2CH_2O)_{20}H$) | 1.0 part by mass |
| Propylene glycol | 14.8 parts by mass |

A coating liquid for an alignment layer having the following composition was continuously applied to the support using a #14 wire bar.

Next, the support on which the coating film was formed was dried using hot air at 60° C. for 60 seconds and was dried using hot air at 100° C. for 120 seconds.

Next, the dried coating film was continuously rubbed to form an alignment layer. At this time, a longitudinal direction and a transport direction of the elongated film were parallel to each other, and a rotation axis of a rubbing roller was shifted clockwise from the film longitudinal direction by 45°.

| (Coating Liquid for Alignment Layer) | |
|---|---|
| The following modified polyvinyl alcohol | 10.0 parts by mass |
| Water | 371.0 parts by mass |
| Methanol | 119.0 parts by mass |
| Glutaraldehyde | 0.5 parts by mass |
| Polymerization initiator (IRGACURE 2959, manufactured by BASF SE) | 0.3 part by mass |

Modified Polyvinyl Alcohol (In the Following Structural Formula, the Ratio is a Molar Ratio)

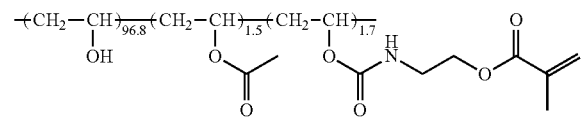

The following coating liquid 1 for an optically-anisotropic layer was prepared.

| (Coating Liquid 1 for Optically-Anisotropic Layer) | |
|---|---|
| The following liquid crystal compound L-1 | 80 parts by mass |
| Infrared absorbing colorant IR-1 | 20 parts by mass |
| Photopolymerization initiator 1 (IRGACURE OXE01, manufactured by BASF SE) | 3.0 parts by mass |
| Photopolymerization initiator 2 (IRGACURE 184, manufactured by BASF SE) | 3.0 parts by mass |
| The following fluorine-containing compound F-1 | 0.2 parts by mass |
| Cyclopentanone | 227.1 parts by mass |

Liquid Crystal Compound L-1 (A Mixture of the Following Three Kinds of Compounds; A Mixing Ratio is Described on the Upper Left Side of the Compound)

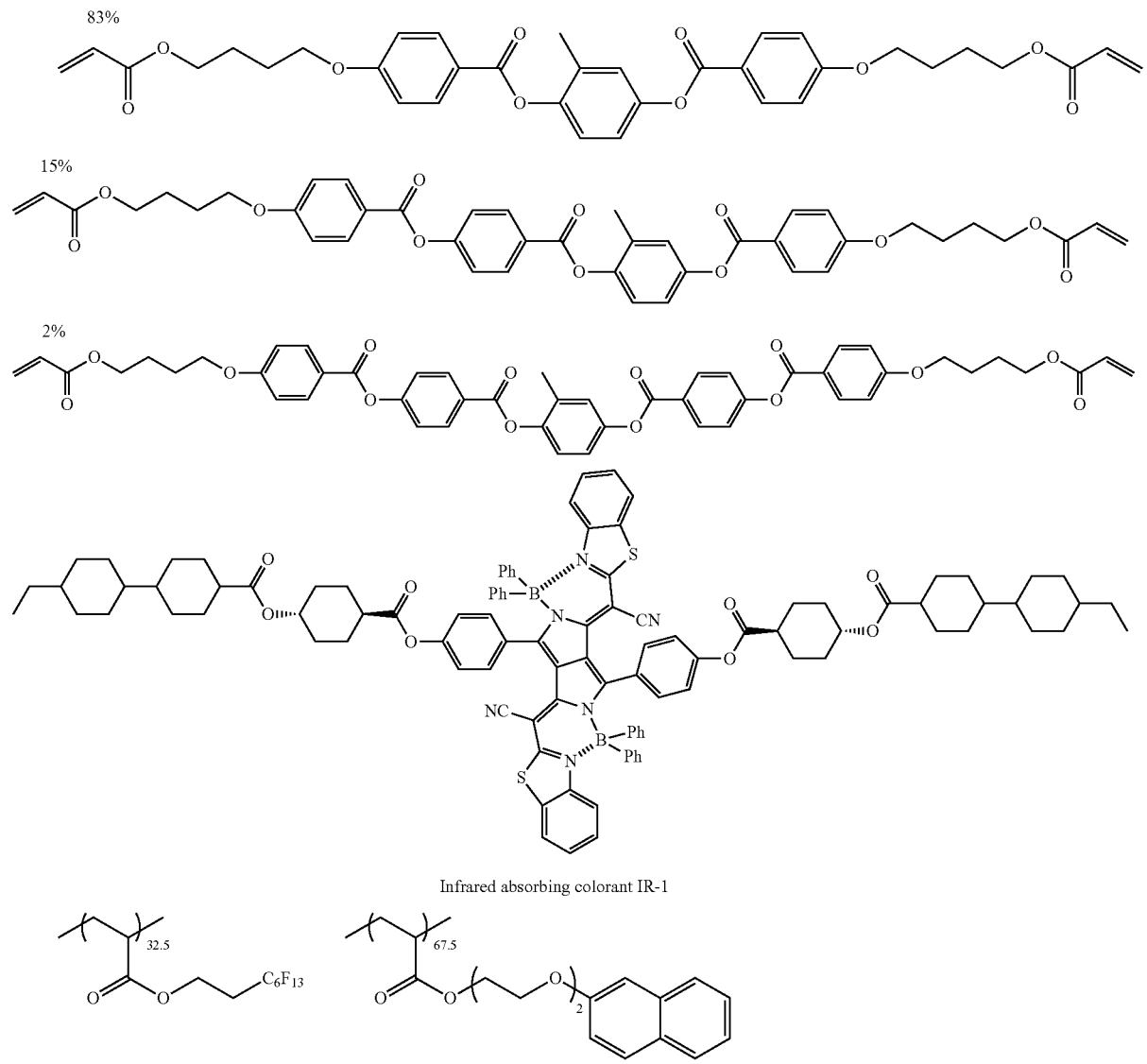

Infrared absorbing colorant IR-1

Fluorine-containing compound F-1

The coating liquid 1 for an optically-anisotropic layer was applied to the alignment layer using a wire bar to form a coating film, and the coating film was heated at 100° C. for 5 minutes and cooled to 60° C.

Next, nitrogen purge was performed so as to obtain an atmosphere where the oxygen concentration was 1.0 vol % or less, and the coating film was radiated with ultraviolet light at an irradiation dose of 500 mJ/cm$^2$ using a high pressure mercury lamp to prepare an optical element. The thickness of the obtained optical element (excluding the support and the alignment layer) was 5 μm.

[Characteristic Evaluation of Optical Element]

The absorption anisotropy of the optical element prepared in Example 1 was acquired by measuring the polar angle dependence of polarization characteristics. Specifically, by using Axoscan (manufactured by Axometrics, Inc.) as a measuring device, at an azimuthal angle (azimuthal angle indicated by a broken line in FIG. 9) orthogonal to the absorption axis, a Mueller matrix is measured while the normal direction polar angle in a range of −50° to 0° at an interval of 10°, and the degree of absorption anisotropy, that is, kz−kx is obtained by fitting. The result was kz−kx=0. Note that kx represents an absorbance in the in-plane absorption axis, and kz represents an absorbance in an out-of-plane direction.

[Simulation of Effect in Fingerprint Recognition System]

Based on the result of light-transmitting properties measured by the optical element prepared in Example 1, the result obtained by performing the same measurement using a commercially available louver film [manufactured by 3M, trade name: a privacy film (PF12.1WS), thickness: 143 μm], and the result of expecting light-transmitting properties assuming that the thickness of the louver film was reduced to 10 μm while maintaining the film internal structure, the effect of improving the S/N ratio in the fingerprint recognition system was simulated in the following manner.

It was assumed that a fingerprint was approximated to an one-dimensional structure, the length of an protrusion portion was 400 μm, the reflectivity of the protrusion portion was 1, the length of a recess portion was 100 μm, and the reflectivity of the recess portion was 0.1.

In addition, it was assumed that reflection (here, the angular directivity of the reflected light was assumed as σ of the normal distribution=15°) from the virtual fingerprint occurred uniformly at an interval of 5 μm.

A detection system of the fingerprint recognition system for performing detection at an interval of 5 μm on a detection surface 300 μm distant from the virtual fingerprint was assumed.

In the detection system of the fingerprint recognition system, assuming that the optical element prepared in Example 1, the commercially available louver film, or the louver film obtained by reducing the thickness to 10 μm was provided between the fingerprint portion and the detection surface, the S/N ratio of signal light that reached the detection surface from the fingerprint was calculated.

Note that the angular directivity of the louver film obtained by reducing the thickness to 10 μm was calculated assuming that the angular directivity has linearity with the structural angle of the louver.

In addition, in a case where nothing was provided between the fingerprint portion and the detection surface, the S/N ratio was calculated using the same method.

The result of the S/N ratio shown below was a value obtained by dividing the intensity of noise light by the intensity of signal light.

<Result of S/N Ratio>

A case where nothing was provided: 4.7

A case where the optical element according to Example 1 was provided: 8.4

A case where the commercially available louver film was provided: 9.1

A case where the virtual louver having a thickness of 10 μm was provided: 5.0

The above result showed that the optical element according to the embodiment of the present invention can realize the fingerprint recognition system having a smaller thickness than the commercially available louver and having an excellent S/N ratio.

Example 2

An optical element was prepared using the same method as that of Example 1, the following coating liquid 2 for an optically-anisotropic film was used instead of the coating liquid 1 for an optically-anisotropic film. The thickness of the obtained optical element (excluding the support and the alignment layer) was 5 μm.

| (Coating Liquid 2 for Optically-Anisotropic Film) | |
|---|---|
| The following liquid crystal compound D-1 | 100 parts by mass |
| The following infrared absorbing colorant IR-2 | 5 parts by mass |
| Photopolymerization initiator IRGACURE 907 (manufactured by BASF SE) | 3 parts by mass |
| The following fluorine-containing compound F-2 (air interface alignment agent) | 0.25 parts by mass |
| The following additive T-1 | 0.9 parts by mass |
| Methyl ethyl ketone | 360 parts by mass |

Liquid Crystal Compound D-1 (A Mixture of the Following Two Kinds of Compounds)

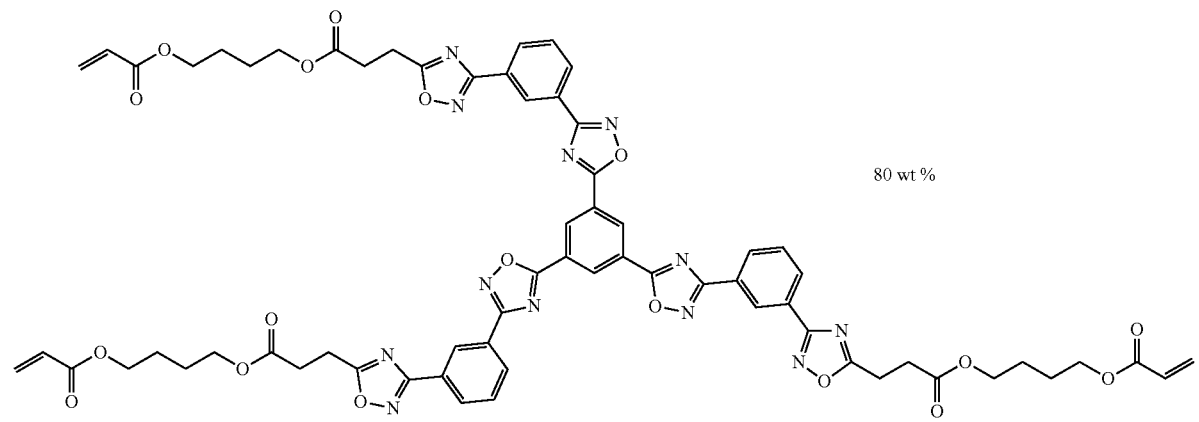

80 wt %

-continued
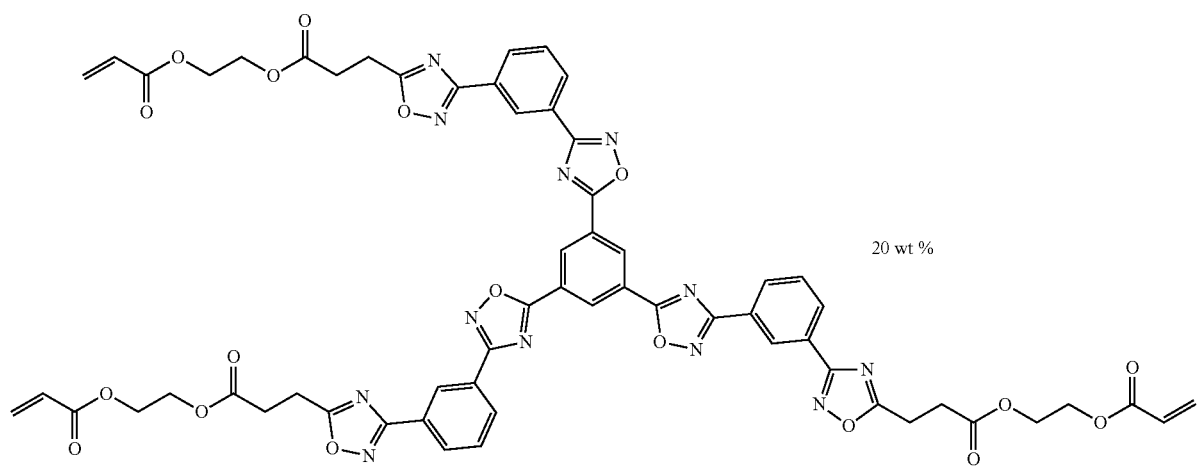
20 wt %
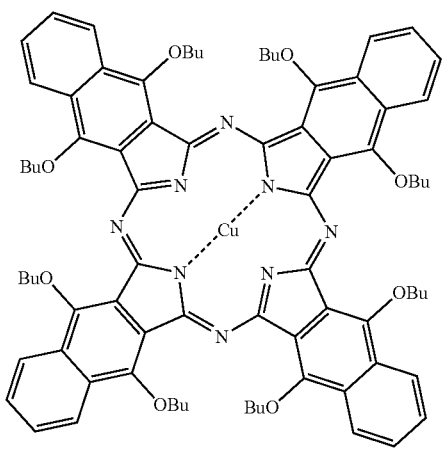
Infrared absorbing colorant IR-2
(maximal absorption wavelength: 867 nm)
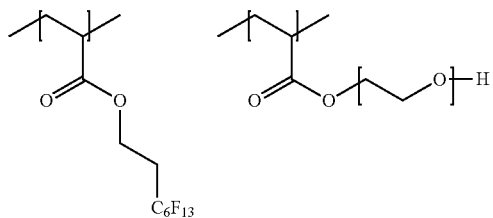
Fluorine-conatining compound F-2
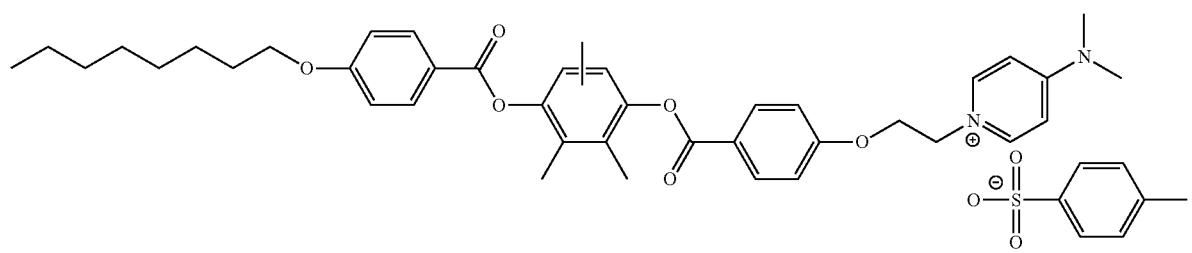
Additive T-1

Example 3

An optical element was prepared using the same method as that of Example 2, except that the infrared absorbing colorant IR-2 was changed to EXCOLOR series IR-10A (maximal absorption wavelength: 852 nm; manufactured by Nippon Shokubai Co., Ltd.). The thickness of the obtained optical element (excluding the support and the alignment layer) was 5 μm.

Example 4

An optical element was prepared using the same method as that of Example 2, except that the infrared absorbing colorant IR-2 was changed to EXCOLOR series IR-14 (maximal absorption wavelength: 844 nm; manufactured by Nippon Shokubai Co., Ltd.). The thickness of the obtained optical element (excluding the support and the alignment layer) was 5 μm.

Example 5

An optical element was prepared using the same method as that of Example 2, except that the infrared absorbing colorant IR-2 was changed to EXCOLOR series HA-1 (maximal absorption wavelength: 942 nm; manufactured by Nippon Shokubai Co., Ltd.). The thickness of the obtained optical element (excluding the support and the alignment layer) was 5 μm.

Example 6

An optical element was prepared using the same method as that of Example 2, except that the support was changed to a glass substrate, the alignment layer was changed to SE-130 (manufactured by Nissan Chemical Industries Ltd.), and the additive T-1 was not used in the coating liquid 2 for an optically-anisotropic film. The thickness of the obtained optical element (excluding the glass substrate and the alignment layer) was 5 μm.

Example 7

An optical element was prepared using the same method as that of Example 2, except that the alignment layer was changed to a photo-alignment film (LPP-JP265CP, manufactured by Rolic Technologies Ltd.), and the additive T-1 was not used in the coating liquid 2 for an optically-anisotropic film. The thickness of the obtained optical element (excluding the support and the photo-alignment film) was 5 μm.

Example 8

An optical film A was prepared using the same method as that of Example 1, except that the following infrared absorbing colorant IR-3 was used instead of the infrared absorbing colorant IR-1. The thickness of the obtained optical film A (excluding the support and the alignment layer) was 5 μm.

Infrared Absorbing Colorant IR-3 (Maximal Absorption Wavelength: 840 nm)

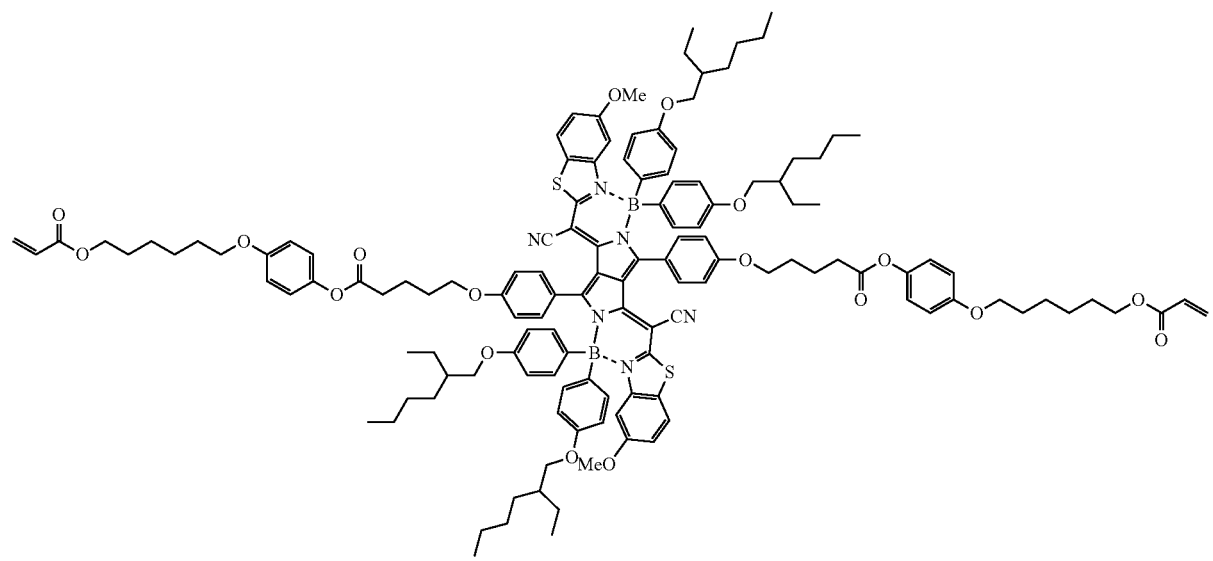

An optical film B was prepared using the same method as that of Example 1, the following coating liquid 3 for an optically-anisotropic film was used instead of the coating liquid 1 for an optically-anisotropic film. The thickness of the obtained optical film B (excluding the support and the alignment layer) was 5 μm.

Next, the optical film A and the optical film B were laminated to prepare an optical element.

| (Coating Liquid 3 for Optically-Anisotropic Film) | |
|---|---|
| The following liquid crystal compound L-1 | 80 parts by mass |
| Infrared absorbing colorant IR-3 | 20 parts by mass |
| Photopolymerization initiator 1 (IRGACURE OXE01, manufactured by BASF SE) | 3.0 parts by mass |
| Photopolymerization initiator 2 (IRGACURE 184, manufactured by BASF SE) | 3.0 parts by mass |
| The following alignment agent D1 | 1.48 parts by mass |
| The following alignment agent D2 | 1.48 parts by mass |
| Cyclopentanone | 227.1 parts by mass |

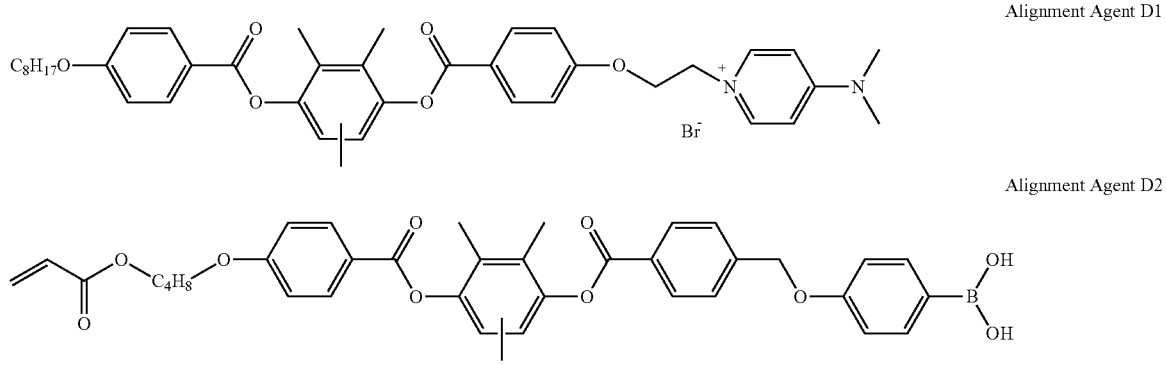

Alignment Agent D1

Alignment Agent D2

The absorption anisotropy of the optical element prepared in each of Examples 1 to 8 was acquired by measuring the polar angle dependence of polarization characteristics. Specifically, by using Axoscan (manufactured by Axometrics, Inc.) as a measuring device, at an azimuthal angle (azimuthal angle indicated by a broken line in FIG. 9) orthogonal to the absorption axis, a Mueller matrix is measured while the normal direction polar angle in a range of −50° to 0° at an interval of 10°, and the degree of absorption anisotropy, that is, kz−kx is obtained by fitting. All of the results were kz−kx=0. Note that kx represents an absorbance in the in-plane absorption axis, and kz represents an absorbance in an out-of-plane direction.

Regarding each of the optical elements prepared in Examples 2 to 8, the same simulation as that of Example 1 was performed to evaluate the S/N ratio.

In addition, the dichroic ratio in the in-plane direction was measured using the above-described method.

In addition, the color was checked by visual inspection. Regarding the neutral gray, whether or not coordinate values L, a, and b satisfied 22≤L≤70, −2.0≤a≤2.0, and −2.0≤b≤2.0, respectively, and whether or not an average value of spectroscopic transmittance in a wavelength of 400 to 700 nm was within ±30% were checked.

The results are shown in Table 1 below.

TABLE 1

| | S/N Ratio | Dichroic Ratio | Color |
|---|---|---|---|
| Example 2 | 8.3 | 9.5 | Orange |
| Example 3 | 8.1 | 8.5 | Neutral Gray |
| Example 4 | 7.5 | 7.8 | Neutral Gray |
| Example 5 | 8.2 | 9.0 | Neutral Gray |
| Example 6 | 8.3 | 9.8 | Orange |
| Example 7 | 8.4 | 10.5 | Orange |
| Example 8 | 8.3 | 9.6 | Green |

The above result in Table 1 showed that as in Example 1, the optical elements prepared in Examples 2 to 8 can realize the fingerprint recognition system having a smaller thickness than the commercially available louver and having an excellent S/N ratio.

In addition, it was found that, in Examples 3 to 5, the color was neutral gray and the optical elements were particularly suitable for the use of the fingerprint recognition sensor.

EXPLANATION OF REFERENCES

12: substrate
14A: first light emitting element
14B: second light emitting element
16A: first light-receiving element
16B: second light-receiving element
18: optical element
20: first layer 22: second layer
10A, 10B, 100: fingerprint recognition sensor
100A: surface
F: finger
N: near infrared absorbing dichroic substance
S: stray light

What is claimed is:

1. A fingerprint recognition sensor comprising:
a light-receiving element; and
an optical element that includes a near infrared absorbing dichroic substance,
wherein a fingerprint reading surface is positioned on a side of the optical element opposite to the light-receiving element side,
the optical element has an absorption axis with respect to near infrared light in an in-plane direction, and
in a case where linearly polarized light of near infrared light orthogonal to the absorption axis is radiated from a normal direction of the optical element and from a direction inclined by 45° from the normal direction at an azimuthal angle orthogonal to the absorption axis, an absorbance during the radiation from the direction inclined by 45° from the normal direction is more than an absorbance during the radiation from the normal direction.

2. The fingerprint recognition sensor according to claim 1, wherein the optical element includes a first layer that includes a near infrared absorbing dichroic substance and has an absorption axis with respect to near infrared light in an in-plane direction and a second layer that includes a near infrared absorbing dichroic substance and has an absorption axis with respect to near infrared light in a thickness direction.

3. The fingerprint recognition sensor according to claim 2, wherein the first layer and the second layer are layers that do not substantially absorb visible light.

4. The fingerprint recognition sensor according to claim 1, wherein the optical element consists of a single layer that includes a near infrared absorbing dichroic substance and has an absorption axis with respect to near infrared light in an in-plane direction, and
in a cross-section taken along the absorption axis, the optical element does not have absorption anisotropy with respect to near infrared light.

5. The fingerprint recognition sensor according to claim 4, wherein the near infrared absorbing dichroic substance is a substance that does not substantially absorb visible light.

6. The fingerprint recognition sensor according to claim 4, wherein the near infrared absorbing dichroic substance is a disk-like colorant.

7. The fingerprint recognition sensor according to claim 5, wherein the near infrared absorbing dichroic substance is a disk-like colorant.

* * * * *